United States Patent
Magyar et al.

(10) Patent No.: US 11,957,542 B2
(45) Date of Patent: Apr. 16, 2024

(54) SENSING COMPLETE INJECTION FOR ANIMAL INJECTION DEVICE

(71) Applicant: Automed Patent Holdco LLC, Loveland, CO (US)

(72) Inventors: Luke Magyar, Ames, IA (US); David Royce Edwards, Ames, IA (US)

(73) Assignee: Automed Patent Holdco, LLC, Loveland, CO (US)

( * ) Notice: Subject to any disclaimer, the term of this patent is extended or adjusted under 35 U.S.C. 154(b) by 495 days.

(21) Appl. No.: 16/863,423

(22) Filed: Apr. 30, 2020

(65) Prior Publication Data
US 2021/0338402 A1   Nov. 4, 2021

(51) Int. Cl.
*G08B 21/04* (2006.01)
*A61D 7/00* (2006.01)
(Continued)

(52) U.S. Cl.
CPC ............. *A61D 7/00* (2013.01); *A61M 5/1452* (2013.01); *A61M 5/30* (2013.01); *A61M 5/31568* (2013.01); *A61M 5/365* (2013.01); *G16H 20/17* (2018.01); *G16H 40/40* (2018.01); *G16H 40/67* (2018.01); *G16H 50/20* (2018.01); *A61J 7/0053* (2013.01); *A61M 31/00* (2013.01); *A61M 2205/13* (2013.01); *A61M 2205/16* (2013.01); *A61M 2205/18* (2013.01); *A61M 2205/332* (2013.01); *A61M 2205/3327* (2013.01); *A61M 2205/3584* (2013.01); *A61M 2205/502* (2013.01); *A61M 2205/6054* (2013.01); *A61M 2210/0618* (2013.01); *A61M 2250/00* (2013.01)

(58) Field of Classification Search
USPC ......... 340/539.12, 525, 539.24, 539.29, 575, 340/578, 618, 644, 686.1, 691.6, 825.19
See application file for complete search history.

(56) References Cited

U.S. PATENT DOCUMENTS 3,941,130 A    3/1976   Tibbs
4,073,321 A    2/1978   Moskowitz
(Continued)

FOREIGN PATENT DOCUMENTS

CA    2267812 A1   10/2000
EP    3236882 B1    2/2020
(Continued)

OTHER PUBLICATIONS

International Preliminary Report on Patentabitlity dated Jan. 10, 2014 for International Application No. PCT/AU2014/000014 (7 Pages).
(Continued)

*Primary Examiner* — Daniel Previl

(57) ABSTRACT

A semi-automated veterinary medicine delivery device may sense whether and how much air may have been incorporated into a dose delivered to an animal. The device may also sense an incomplete injection in some cases, and may cause a second dose to be administered to make up for the incomplete dose. The device may compare a position sensor on a syringe in combination with a current sensor on a motor attached to the syringe to detect any abnormalities. In the case of an improper dose, the device may alert the user and administer a second dose.

7 Claims, 9 Drawing Sheets

(51) Int. Cl.
*A61M 5/145* (2006.01)
*A61M 5/30* (2006.01)
*A61M 5/315* (2006.01)
*A61M 5/36* (2006.01)
*G16H 20/17* (2018.01)
*G16H 40/40* (2018.01)
*G16H 40/67* (2018.01)
*G16H 50/20* (2018.01)
*A61J 7/00* (2006.01)
*A61M 31/00* (2006.01)

(56) References Cited

U.S. PATENT DOCUMENTS

| | | |
|---|---|---|
| 4,103,684 A | 8/1978 | Ismach |
| 4,106,770 A | 8/1978 | Gray |
| 4,261,358 A | 4/1981 | Vargas et al. |
| 4,275,729 A | 6/1981 | Silver et al. |
| 4,316,463 A | 2/1982 | Schmitz et al. |
| 4,475,905 A | 10/1984 | Himmelstrup |
| 4,498,904 A | 2/1985 | Turner et al. |
| 4,547,189 A | 10/1985 | Moore, Jr. |
| 4,592,742 A | 6/1986 | Landau |
| 4,664,653 A | 5/1987 | Sagstetter et al. |
| 4,710,162 A | 12/1987 | Johnson |
| 4,735,611 A | 4/1988 | Anderson et al. |
| 4,738,660 A | 4/1988 | Lucas |
| 4,852,768 A | 8/1989 | Bartsch |
| 4,858,607 A | 8/1989 | Jordan et al. |
| 4,865,591 A | 9/1989 | Sams |
| 4,902,279 A | 2/1990 | Schmidtz et al. |
| 4,955,868 A | 9/1990 | Klein |
| 4,988,339 A | 1/1991 | Vadher |
| 4,994,034 A | 2/1991 | Botich et al. |
| 5,011,476 A | 4/1991 | Foster |
| 5,026,349 A | 6/1991 | Schmitz et al. |
| 5,127,906 A | 7/1992 | Landry, Jr. et al. |
| 5,151,088 A | 9/1992 | Allison et al. |
| 5,163,908 A | 11/1992 | Lambert |
| 5,176,643 A | 1/1993 | Kramer et al. |
| 5,190,526 A | 3/1993 | Murray et al. |
| 5,201,720 A | 4/1993 | Borgia et al. |
| 5,226,896 A | 7/1993 | Harris |
| 5,232,459 A | 8/1993 | Hjertman |
| 5,267,963 A | 12/1993 | Bachynsky |
| 5,271,744 A | 12/1993 | Kramer et al. |
| 5,298,024 A | 3/1994 | Richmond |
| 5,300,041 A | 4/1994 | Haber et al. |
| 5,304,152 A | 4/1994 | Sams |
| 5,320,609 A | 6/1994 | Haber et al. |
| 5,346,480 A | 9/1994 | Hess et al. |
| 5,358,489 A | 10/1994 | Wyrick |
| 5,364,362 A | 11/1994 | Schulz |
| 5,391,157 A | 2/1995 | Harris et al. |
| 5,411,487 A | 5/1995 | Castagna |
| 5,451,210 A | 9/1995 | Kramer et al. |
| 5,514,097 A | 5/1996 | Knauer |
| 5,545,147 A | 8/1996 | Harris |
| 5,560,317 A | 10/1996 | Bunyan et al. |
| 5,562,626 A | 10/1996 | Sanpietro |
| 5,573,513 A | 11/1996 | Wozencroft |
| 5,599,309 A | 2/1997 | Marshall et al. |
| 5,620,421 A | 4/1997 | Schmitz |
| 5,626,566 A | 5/1997 | Petersen et al. |
| 5,695,472 A | 12/1997 | Wyrick |
| 5,713,871 A | 2/1998 | Stock |
| 5,722,956 A | 3/1998 | Sims et al. |
| 5,769,822 A | 6/1998 | McGary et al. |
| 5,776,107 A | 7/1998 | Cherif-Cheikh |
| 5,779,677 A | 7/1998 | Frezza |
| 5,792,117 A | 8/1998 | Brown |
| 5,800,403 A | 9/1998 | Pressly et al. |
| 5,833,669 A | 11/1998 | Wyrick |
| 5,882,342 A | 3/1999 | Cooper et al. |
| 5,911,703 A | 6/1999 | Slate et al. |
| 5,921,959 A | 7/1999 | McGary et al. |
| 5,984,900 A | 11/1999 | Mikkelsen |
| 5,984,906 A | 11/1999 | Bonnichsen et al. |
| 5,997,500 A | 12/1999 | Cook et al. |
| 6,015,438 A | 1/2000 | Shaw |
| 6,056,716 A | 5/2000 | D'Antonio et al. |
| 6,068,615 A | 5/2000 | Brown et al. |
| 6,077,247 A | 6/2000 | Marshall et al. |
| 6,083,199 A | 7/2000 | Thorley et al. |
| 6,086,567 A | 7/2000 | Kirchhofer et al. |
| 6,099,504 A | 8/2000 | Gross et al. |
| 6,102,896 A | 8/2000 | Roser |
| 6,110,147 A | 8/2000 | Perouse |
| 6,171,285 B1 | 1/2001 | Johnson |
| 6,179,812 B1 | 1/2001 | Botich et al. |
| 6,203,530 B1 | 3/2001 | Stewart |
| 6,221,044 B1 | 4/2001 | Greco |
| 6,270,479 B1 | 8/2001 | Bergens et al. |
| 6,277,101 B1 | 8/2001 | Kirchhofer et al. |
| 6,312,412 B1 | 11/2001 | Saied et al. |
| 6,319,234 B1 | 11/2001 | Restelli et al. |
| 6,368,303 B1 | 4/2002 | Caizza |
| 6,387,078 B1 | 5/2002 | Gillespie, III |
| 6,391,003 B1 | 5/2002 | Lesch, Jr. |
| 6,398,762 B1 | 6/2002 | Vetter et al. |
| 6,413,237 B1 | 7/2002 | Caizza et al. |
| 6,428,528 B2 | 8/2002 | Sadowski et al. |
| 6,432,087 B1 | 8/2002 | Hoeck et al. |
| 6,461,333 B1 | 10/2002 | Frezza |
| 6,482,176 B1 | 11/2002 | Wich |
| 6,482,185 B1 | 11/2002 | Hartmann |
| 6,511,460 B1 | 1/2003 | Arnissolle |
| 6,530,903 B2 | 3/2003 | Wang et al. |
| 6,547,764 B2 | 4/2003 | Larsen et al. |
| 6,558,352 B1 | 5/2003 | Hogan |
| 6,558,357 B1 | 5/2003 | Hoeck |
| 6,565,538 B2 | 5/2003 | Quinn et al. |
| 6,569,123 B2 | 5/2003 | Alchas et al. |
| 6,569,143 B2 | 5/2003 | Alchas et al. |
| 6,589,210 B1 | 7/2003 | Rolfe |
| 6,599,272 B1 | 7/2003 | Hjertman et al. |
| 6,605,058 B1 | 8/2003 | Wich |
| 6,607,508 B2 | 8/2003 | Knauer |
| 6,610,042 B2 | 8/2003 | Leon et al. |
| 6,638,255 B1 | 10/2003 | Weber |
| 6,648,858 B2 | 11/2003 | Asbaghi |
| 6,652,483 B2 | 11/2003 | Slate et al. |
| 6,656,163 B1 | 12/2003 | Marshall et al. |
| 6,656,164 B1 | 12/2003 | Smith |
| 6,689,118 B2 | 2/2004 | Alchas et al. |
| 6,692,463 B1 | 2/2004 | Marteau et al. |
| 6,692,469 B1 | 2/2004 | Weekes et al. |
| 6,699,220 B2 | 3/2004 | Rolfe |
| 6,726,661 B2 | 4/2004 | Munk et al. |
| 6,776,776 B2 | 8/2004 | Alchas et al. |
| 6,789,467 B2 | 9/2004 | Johnston et al. |
| 6,805,686 B1 | 10/2004 | Fathallah et al. |
| 6,808,507 B2 | 10/2004 | Roser |
| 6,817,989 B2 | 11/2004 | Svendsen et al. |
| 6,843,781 B2 | 1/2005 | Alchas et al. |
| 6,858,020 B2 | 2/2005 | Rusnak |
| 6,890,319 B1 | 5/2005 | Crocker |
| 6,976,976 B2 | 12/2005 | Doyle |
| 6,979,316 B1 | 12/2005 | Rubin et al. |
| 7,011,649 B2 | 3/2006 | Semna et al. |
| 7,056,307 B2 | 6/2006 | Smith et al. |
| 7,097,634 B2 | 8/2006 | Gilbert |
| 7,104,969 B2 | 9/2006 | Plessis |
| 7,112,187 B2 | 9/2006 | Karlsson |
| 7,217,253 B2 | 5/2007 | Slate et al. |
| 7,229,432 B2 | 6/2007 | Marshall et al. |
| 7,241,278 B2 | 7/2007 | Møller |
| 7,247,151 B2 | 7/2007 | Slawson |
| 7,252,651 B2 | 8/2007 | Haider et al. |
| 7,341,574 B2 | 3/2008 | Schreijag |
| 7,425,204 B2 | 9/2008 | Angel et al. |
| 7,500,963 B2 | 3/2009 | Westbye et al. |
| 7,500,967 B2 | 3/2009 | Thorley et al. |
| 7,597,685 B2 | 10/2009 | Olson |

(56) References Cited

U.S. PATENT DOCUMENTS

| | | |
|---|---|---|
| 7,615,234 B2 | 11/2009 | Potter et al. |
| 7,621,891 B2 | 11/2009 | Wyrick |
| 7,637,891 B2 | 12/2009 | Wall |
| 7,645,265 B2 | 1/2010 | Stamp |
| 7,670,314 B2 | 3/2010 | Wall et al. |
| 7,674,246 B2 | 3/2010 | Gillespie et al. |
| 7,721,674 B2 | 5/2010 | Smith |
| 7,727,201 B2 | 6/2010 | Kirchhofer |
| 7,785,292 B2 | 8/2010 | Harrison |
| RE41,956 E | 11/2010 | Klitgaard et al. |
| 7,824,360 B2 | 11/2010 | Azar et al. |
| 7,896,850 B2 | 3/2011 | Kronestedt et al. |
| 7,905,352 B2 | 3/2011 | Wyrick |
| 7,918,824 B2 | 4/2011 | Bishop et al. |
| 7,935,087 B2 | 5/2011 | Judd et al. |
| 7,976,509 B2 | 7/2011 | Moser et al. |
| 7,976,510 B2 | 7/2011 | Janish et al. |
| 7,981,088 B2 | 7/2011 | Westbye et al. |
| 7,988,660 B2 | 8/2011 | Byland et al. |
| 7,988,675 B2 | 8/2011 | Gillespie, III et al. |
| 8,002,745 B2 | 8/2011 | Kaal et al. |
| 8,012,131 B2 | 9/2011 | Moser et al. |
| 8,016,789 B2 | 9/2011 | Grant et al. |
| 8,021,333 B2 | 9/2011 | Kaal et al. |
| 8,021,335 B2 | 9/2011 | Lesch, Jr. |
| 8,052,645 B2 | 11/2011 | Slate et al. |
| 8,052,655 B2 | 11/2011 | Møller et al. |
| 8,114,050 B2 | 2/2012 | Kaal et al. |
| 8,172,813 B2 | 5/2012 | Janish |
| 8,177,749 B2 | 5/2012 | Slate et al. |
| 8,182,444 B2 | 5/2012 | Uber, III et al. |
| 8,187,226 B2 | 5/2012 | Stamp et al. |
| 8,197,450 B2 | 6/2012 | Glejbol et al. |
| 8,201,518 B2 | 6/2012 | Smith |
| 8,267,890 B2 | 9/2012 | Alchas et al. |
| 8,298,194 B2 | 10/2012 | Møller |
| 8,308,687 B2 | 11/2012 | Carrel et al. |
| 8,343,103 B2 | 1/2013 | Moser |
| 8,353,878 B2 | 1/2013 | Moller et al. |
| 8,357,120 B2 | 1/2013 | Moller et al. |
| 8,361,036 B2 | 1/2013 | Møller et al. |
| 8,366,682 B2 | 2/2013 | Wyrick |
| 8,376,993 B2 | 2/2013 | Cox et al. |
| 8,409,141 B2 | 4/2013 | Johansen et al. |
| 8,439,876 B2 | 5/2013 | Spohn et al. |
| 8,496,646 B2 | 7/2013 | Kamen et al. |
| 8,567,235 B2 | 10/2013 | Bojan et al. |
| 8,585,377 B2 | 11/2013 | Kamen et al. |
| 8,608,708 B2 | 12/2013 | Cowe |
| 8,636,704 B2 | 1/2014 | Shang et al. |
| 8,652,095 B2 | 2/2014 | Chaturvedi et al. |
| 8,734,403 B2 | 5/2014 | Hirschel et al. |
| 8,784,381 B2 | 7/2014 | Watanabe et al. |
| 8,864,726 B2 | 10/2014 | Halili et al. |
| 8,900,197 B2 | 12/2014 | Crow |
| 8,905,970 B2 | 12/2014 | Bates et al. |
| 8,913,123 B2 | 12/2014 | Miller |
| 8,915,886 B2 | 12/2014 | Cowe |
| 8,920,374 B2 | 12/2014 | Bokelman et al. |
| 8,932,254 B2 | 1/2015 | Eaton |
| 8,932,266 B2 | 1/2015 | Wozencroft |
| 8,945,051 B2 | 2/2015 | Stokes, Jr. et al. |
| 8,945,063 B2 | 2/2015 | Wotton et al. |
| 8,992,484 B2 | 3/2015 | Radmer et al. |
| 8,998,855 B2 | 4/2015 | Hudson et al. |
| 9,011,386 B2 | 4/2015 | Kronestedt et al. |
| 9,017,293 B2 | 4/2015 | Edhouse et al. |
| 9,022,989 B2 | 5/2015 | Bicknell et al. |
| 9,044,378 B2 | 6/2015 | Verespej et al. |
| 9,044,553 B2 | 6/2015 | James et al. |
| 9,101,722 B2 | 8/2015 | Moller |
| 9,108,006 B2 | 8/2015 | Jensen et al. |
| 9,114,212 B2 | 8/2015 | Enggaard et al. |
| 9,114,216 B2 | 8/2015 | Sutkin et al. |
| 9,138,542 B2 | 9/2015 | Smith |
| 9,144,648 B2 | 9/2015 | Lesch, Jr. et al. |
| 9,149,575 B2 | 10/2015 | Cabiri |
| 9,155,844 B2 | 10/2015 | Brereton et al. |
| 9,173,997 B2 | 11/2015 | Gross et al. |
| 9,192,727 B2 | 11/2015 | Møller et al. |
| 9,199,039 B2 | 12/2015 | Moser et al. |
| 9,199,041 B2 | 12/2015 | Edginton |
| 9,216,256 B2 | 12/2015 | Olson et al. |
| 9,233,213 B2 | 1/2016 | Olson et al. |
| 9,233,215 B2 | 1/2016 | Hourmand et al. |
| 9,248,245 B2 | 2/2016 | Ekman et al. |
| 9,314,565 B2 | 4/2016 | Spohn et al. |
| 9,333,309 B2 | 5/2016 | Sadowski et al. |
| 9,339,609 B2 | 5/2016 | Ekman et al. |
| 9,352,089 B2 | 5/2016 | Hourmand et al. |
| 9,379,652 B2 | 6/2016 | Favreau |
| 9,381,308 B2 | 7/2016 | Hemmann et al. |
| 9,402,949 B2 | 8/2016 | Tieck et al. |
| 9,402,954 B1 | 8/2016 | Slevin |
| 9,408,973 B2 | 8/2016 | Shang et al. |
| 9,446,204 B2 | 9/2016 | Teucher et al. |
| 9,452,261 B2 | 9/2016 | Alon |
| 9,457,147 B2 | 10/2016 | Green |
| 9,457,149 B2 | 10/2016 | Kemp et al. |
| 9,457,153 B2 | 10/2016 | Marano, Jr. et al. |
| 9,457,154 B2 | 10/2016 | Moller et al. |
| 9,463,282 B2 | 10/2016 | Barrow-Williams et al. |
| 9,474,866 B2 | 10/2016 | Hourmand et al. |
| 9,486,581 B2 | 11/2016 | Lovell et al. |
| 9,486,583 B2 | 11/2016 | Lannan et al. |
| 9,492,610 B2 | 11/2016 | Cabiri |
| 9,517,311 B2 | 12/2016 | Saiki |
| 9,522,234 B2 | 12/2016 | Cabiri |
| 9,539,392 B2 | 1/2017 | Jennings et al. |
| 9,545,481 B1 | 1/2017 | Rafaat |
| 9,555,190 B2 | 1/2017 | Alderete, Jr. et al. |
| 9,579,468 B2 | 2/2017 | Schoonmaker et al. |
| 9,592,350 B2 | 3/2017 | Roberts et al. |
| 9,616,178 B2 | 4/2017 | Butler et al. |
| 9,629,992 B2 | 4/2017 | Halili et al. |
| 9,656,019 B2 | 5/2017 | Cabiri et al. |
| 9,656,025 B2 | 5/2017 | Boström et al. |
| 9,700,686 B2 | 7/2017 | Gavini et al. |
| 9,724,472 B2 | 8/2017 | Hourmand et al. |
| 9,724,479 B2 | 8/2017 | Sutkin et al. |
| 9,737,667 B2 | 8/2017 | Holmqvist et al. |
| 9,744,297 B2 | 8/2017 | Cabiri et al. |
| 9,744,300 B2 | 8/2017 | Kamen et al. |
| 9,750,885 B2 | 9/2017 | Weaver et al. |
| 9,757,520 B2 | 9/2017 | Corrigan |
| 9,757,523 B2 | 9/2017 | Macdonald et al. |
| 9,764,089 B2 | 9/2017 | Alexandersson |
| 9,764,092 B2 | 9/2017 | Cabiri |
| 9,775,697 B2 | 10/2017 | Buckley et al. |
| 9,795,534 B2 | 10/2017 | Bar-El et al. |
| 9,814,836 B2 | 11/2017 | Cowe |
| 9,821,118 B2 | 11/2017 | Adlon et al. |
| 9,827,373 B2 | 11/2017 | Roervig et al. |
| 9,839,743 B2 | 12/2017 | Lanigan et al. |
| 9,861,759 B2 | 1/2018 | Gross et al. |
| 9,867,949 B2 | 1/2018 | Sund et al. |
| 9,878,091 B2 | 1/2018 | Cabiri |
| 9,889,256 B2 | 2/2018 | Cabiri et al. |
| 9,895,490 B2 | 2/2018 | Kow et al. |
| 9,901,680 B2 | 2/2018 | Roervig et al. |
| 9,901,681 B2 | 2/2018 | Sweeney et al. |
| 9,925,333 B2 | 3/2018 | Hooven et al. |
| 9,931,471 B2 | 4/2018 | Ekman et al. |
| 9,943,649 B2 | 4/2018 | Shang et al. |
| 9,950,112 B2 | 4/2018 | Melker et al. |
| 9,950,125 B2 | 4/2018 | Wotton et al. |
| 9,956,344 B2 | 5/2018 | Cleathero |
| 9,974,904 B2 | 5/2018 | Burk et al. |
| 9,974,905 B2 | 5/2018 | Butler et al. |
| 9,987,420 B2 | 6/2018 | Pananen |
| 9,987,425 B2 | 6/2018 | Alderete et al. |
| 9,987,432 B2 | 6/2018 | Cabiri et al. |
| 10,034,976 B2 | 7/2018 | Vazquez et al. |
| 10,052,436 B2 | 8/2018 | Högdahl |

(56) References Cited

U.S. PATENT DOCUMENTS

| | | | |
|---|---|---|---|
| 10,052,441 B2* | 8/2018 | Searle | A61M 5/482 |
| 10,076,356 B2 | 9/2018 | Hadvary et al. | |
| 10,092,690 B2 | 10/2018 | Gillespie et al. | |
| 10,092,708 B2 | 10/2018 | Thorley et al. | |
| 10,117,996 B2 | 11/2018 | Stefansen | |
| 10,130,768 B2 | 11/2018 | Dungar et al. | |
| 10,143,625 B2 | 12/2018 | Li et al. | |
| 10,159,796 B2 | 12/2018 | Schiff et al. | |
| 10,166,328 B2 | 1/2019 | Oruklu et al. | |
| 10,179,207 B2 | 1/2019 | Haupt | |
| 10,195,341 B2 | 2/2019 | Pananen | |
| 10,195,351 B2 | 2/2019 | Allerdings et al. | |
| 10,226,585 B2 | 3/2019 | Franklin et al. | |
| 10,259,835 B2* | 4/2019 | Siddiqui-Jain | A61P 43/00 |
| 10,265,471 B2 | 4/2019 | Kapas et al. | |
| 10,265,476 B2 | 4/2019 | Laiosa et al. | |
| 10,265,478 B2 | 4/2019 | Kouyoumjian et al. | |
| 10,269,266 B2 | 4/2019 | Rios et al. | |
| 10,279,116 B2 | 5/2019 | Plumptre et al. | |
| 10,279,126 B2 | 5/2019 | Chattaraj et al. | |
| 10,300,201 B2 | 5/2019 | Lumme et al. | |
| 10,300,206 B2 | 5/2019 | Bergens et al. | |
| 10,335,545 B2 | 7/2019 | Cabiri | |
| 10,376,641 B2 | 8/2019 | Hirschel et al. | |
| 10,376,692 B2 | 8/2019 | Mathiesen et al. | |
| 10,391,252 B2 | 8/2019 | Haupt | |
| 10,391,259 B2 | 8/2019 | Tran et al. | |
| 10,398,837 B2 | 9/2019 | Cabiri et al. | |
| 10,398,842 B2 | 9/2019 | Niven et al. | |
| 10,406,291 B2 | 9/2019 | Hansen et al. | |
| 10,413,667 B2 | 9/2019 | Henderson et al. | |
| 10,413,680 B2 | 9/2019 | Shimizu et al. | |
| 10,512,733 B2 | 12/2019 | Roberts et al. | |
| 10,561,787 B2 | 2/2020 | Kamen et al. | |
| RE47,903 E | 3/2020 | Hourmand et al. | |
| 10,575,767 B2 | 3/2020 | Patel et al. | |
| 10,588,729 B2* | 3/2020 | Moons | A61D 1/025 |
| 10,589,038 B2 | 3/2020 | Chattaraj et al. | |
| 10,596,316 B2 | 3/2020 | Dumas, III et al. | |
| 10,625,026 B2 | 4/2020 | Creaturo | |
| 10,653,830 B2 | 5/2020 | Limaye | |
| 10,661,014 B2 | 5/2020 | Sarkinen et al. | |
| 10,675,415 B2 | 6/2020 | Takabatake et al. | |
| 10,737,030 B2 | 8/2020 | Molson et al. | |
| 10,744,269 B2 | 8/2020 | Veasey et al. | |
| 10,751,483 B2 | 8/2020 | Hatch et al. | |
| 10,888,662 B2 | 1/2021 | Cave | |
| 10,898,648 B2 | 1/2021 | Taylor et al. | |
| 10,912,892 B2 | 2/2021 | Edwards | |
| 10,960,130 B2 | 3/2021 | Schiff et al. | |
| 10,967,127 B2 | 4/2021 | Murakami et al. | |
| 10,995,125 B2* | 5/2021 | Flinspach | A61P 25/04 |
| RE48,593 E | 6/2021 | Hourmand et al. | |
| 11,027,056 B2 | 6/2021 | McMahon | |
| 11,065,386 B2 | 7/2021 | Atterbury et al. | |
| 11,090,441 B2 | 8/2021 | Tran et al. | |
| 11,090,445 B2 | 8/2021 | Diaz et al. | |
| 11,097,053 B2 | 8/2021 | Veyrent et al. | |
| 11,167,086 B2 | 11/2021 | Cabiri et al. | |
| 11,278,677 B2 | 3/2022 | Erbstein et al. | |
| 11,318,252 B2 | 5/2022 | Zhang | |
| 11,357,925 B2 | 6/2022 | Dugand et al. | |
| 11,376,364 B2 | 7/2022 | Dobson et al. | |
| 11,376,373 B2 | 7/2022 | Perot et al. | |
| 11,419,991 B2 | 8/2022 | Diaz et al. | |
| 11,433,186 B2 | 9/2022 | Ulla | |
| 11,439,762 B2 | 9/2022 | Toporek et al. | |
| 11,565,051 B2 | 1/2023 | Helmer | |
| 11,571,518 B2 | 2/2023 | Flather et al. | |
| 11,642,462 B2 | 5/2023 | Stamp | |
| 11,660,397 B2 | 5/2023 | Moeller | |
| 11,672,904 B2 | 6/2023 | Cabiri et al. | |
| 2002/0004652 A1 | 1/2002 | Asbaghi | |
| 2002/0107501 A1 | 8/2002 | Smith et al. | |
| 2002/0161337 A1 | 10/2002 | Shaw et al. | |
| 2002/0188468 A1 | 12/2002 | Hogan | |
| 2003/0023205 A1 | 1/2003 | Botich et al. | |
| 2003/0109833 A1 | 6/2003 | Sharpe | |
| 2003/0114789 A1 | 6/2003 | Haar et al. | |
| 2003/0114799 A1 | 6/2003 | Cheikh | |
| 2004/0035491 A1 | 2/2004 | Castellano | |
| 2004/0068158 A1* | 4/2004 | Bennett | A61M 21/00 600/28 |
| 2004/0133161 A1 | 7/2004 | Trocki et al. | |
| 2004/0143224 A1 | 7/2004 | Field et al. | |
| 2004/0147875 A1 | 7/2004 | Wallace et al. | |
| 2005/0090782 A1 | 4/2005 | Marshall et al. | |
| 2005/0124968 A1 | 6/2005 | Mollhagen | |
| 2005/0171476 A1 | 8/2005 | Judson et al. | |
| 2005/0222539 A1 | 10/2005 | Gonzales et al. | |
| 2006/0069350 A1 | 3/2006 | Buenger et al. | |
| 2006/0069354 A1 | 3/2006 | Buenger et al. | |
| 2006/0129122 A1 | 6/2006 | Wyrick | |
| 2006/0258986 A1 | 11/2006 | Hunter et al. | |
| 2007/0017533 A1 | 1/2007 | Wyrick | |
| 2007/0021716 A1 | 1/2007 | Hansen | |
| 2007/0021720 A1 | 1/2007 | Guillermo | |
| 2007/0203247 A1 | 8/2007 | Phillips et al. | |
| 2007/0265568 A1 | 11/2007 | Tsals et al. | |
| 2008/0009788 A1 | 1/2008 | Hunter et al. | |
| 2008/0147006 A1 | 6/2008 | Brunnberg et al. | |
| 2008/0208142 A1 | 8/2008 | Moller | |
| 2008/0228147 A1 | 9/2008 | David-Hegerich et al. | |
| 2009/0005737 A1 | 1/2009 | Chun | |
| 2009/0112179 A1 | 4/2009 | Zoltan et al. | |
| 2009/0204076 A1 | 8/2009 | Liversidge | |
| 2009/0240210 A1 | 9/2009 | Walton et al. | |
| 2009/0247867 A1 | 10/2009 | Spohn et al. | |
| 2010/0016796 A1 | 1/2010 | Derichs | |
| 2010/0049140 A1 | 2/2010 | Marsh et al. | |
| 2010/0256554 A1 | 10/2010 | Discher, Jr. et al. | |
| 2011/0224613 A1 | 9/2011 | D Antonio et al. | |
| 2011/0226646 A1 | 9/2011 | Wyrick | |
| 2012/0179132 A1 | 7/2012 | Valk et al. | |
| 2012/0233834 A1 | 9/2012 | Szechinski et al. | |
| 2012/0296276 A1 | 11/2012 | Nicholls et al. | |
| 2013/0211337 A1 | 8/2013 | Hofmann | |
| 2013/0274677 A1 | 10/2013 | Ekman et al. | |
| 2013/0331796 A1 | 12/2013 | Wozencroft | |
| 2014/0135705 A1 | 5/2014 | Hourmand et al. | |
| 2014/0248605 A1* | 9/2014 | Loneragan | A61K 39/0275 435/5 |
| 2014/0257236 A1 | 9/2014 | Hemond et al. | |
| 2014/0276583 A1 | 9/2014 | Chen et al. | |
| 2015/0001285 A1 | 1/2015 | Halbert et al. | |
| 2015/0202373 A1 | 7/2015 | Creaturo | |
| 2015/0209515 A1 | 7/2015 | Houde et al. | |
| 2015/0209519 A1 | 7/2015 | Mernøe | |
| 2015/0314068 A1 | 11/2015 | Alderete, Jr. et al. | |
| 2016/0038266 A1 | 2/2016 | Edwards | |
| 2016/0074587 A1 | 3/2016 | Searle et al. | |
| 2016/0266555 A1 | 9/2016 | Favreau | |
| 2016/0303319 A1 | 10/2016 | Tieck et al. | |
| 2017/0000949 A1 | 1/2017 | Franklin et al. | |
| 2017/0072130 A1 | 3/2017 | McMahon | |
| 2017/0348486 A1 | 12/2017 | Andersen et al. | |
| 2017/0361020 A1 | 12/2017 | Font et al. | |
| 2018/0154082 A1* | 6/2018 | Yoh | A61M 5/1782 |
| 2019/0143041 A1 | 5/2019 | Gould | |
| 2019/0175839 A1* | 6/2019 | Kwolek | A61M 5/178 |
| 2020/0023128 A1 | 1/2020 | Fachinger et al. | |
| 2020/0046902 A1 | 2/2020 | Chuang et al. | |
| 2020/0078521 A1 | 3/2020 | Dyer et al. | |
| 2020/0188599 A1 | 6/2020 | Mandaroux et al. | |
| 2021/0236623 A1* | 8/2021 | Georges | C12N 7/00 |
| 2021/0338402 A1 | 11/2021 | Magyar et al. | |

FOREIGN PATENT DOCUMENTS

| | | |
|---|---|---|
| WO | 2007037996 A1 | 4/2007 |
| WO | 2013110624 A3 | 9/2013 |
| WO | 2014107766 A1 | 7/2014 |
| WO | 2014120754 A1 | 8/2014 |
| WO | 2016101031 A1 | 6/2016 |

(56) References Cited

FOREIGN PATENT DOCUMENTS

| WO | 2016180011 A1 | 11/2016 |
| WO | 2019046261 A1 | 3/2019 |
| WO | 2019133648 A1 | 7/2019 |

OTHER PUBLICATIONS

International Search Report dated Jun. 2, 2014 for International Application No. PCT/AU2014/000014 (6 Pages).

* cited by examiner

ECOSYSTEM WITH SEMI-AUTOMATED DOSING DEVICE

SENSING COMPLETE INJECTION FOR ANIMAL INJECTION DEVICE

BACKGROUND

Vaccines, vitamins, medicines, and other substances are routinely administered to livestock. Some substances are injected into the animal intramuscularly, subcutaneously, intradermally, or intravenously. Other substances may be applied by drenching, oral administration, or other methods.

Animal husbandry is often performed by ranch hands in inhospitable environments. Ranch hands may have expertise in managing animals but may not be familiar with veterinary medicine delivery best practices. Further, many injections or medications may be applied in very rugged environments, subject to high heat or low temperatures, dust, dirt, rain, snow, and other weather.

SUMMARY

A semi-automated veterinary medicine delivery device may sense whether and how much air may have been incorporated into a dose delivered to an animal. The device may also sense an incomplete injection in some cases, and may cause a second dose to be administered to make up for the incomplete dose. The device may compare a position sensor on a syringe in combination with a current sensor on a motor attached to the syringe to detect any abnormalities. In the case of an improper dose, the device may alert the user and administer a second dose.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

DETAILED DESCRIPTION

Figure 1:
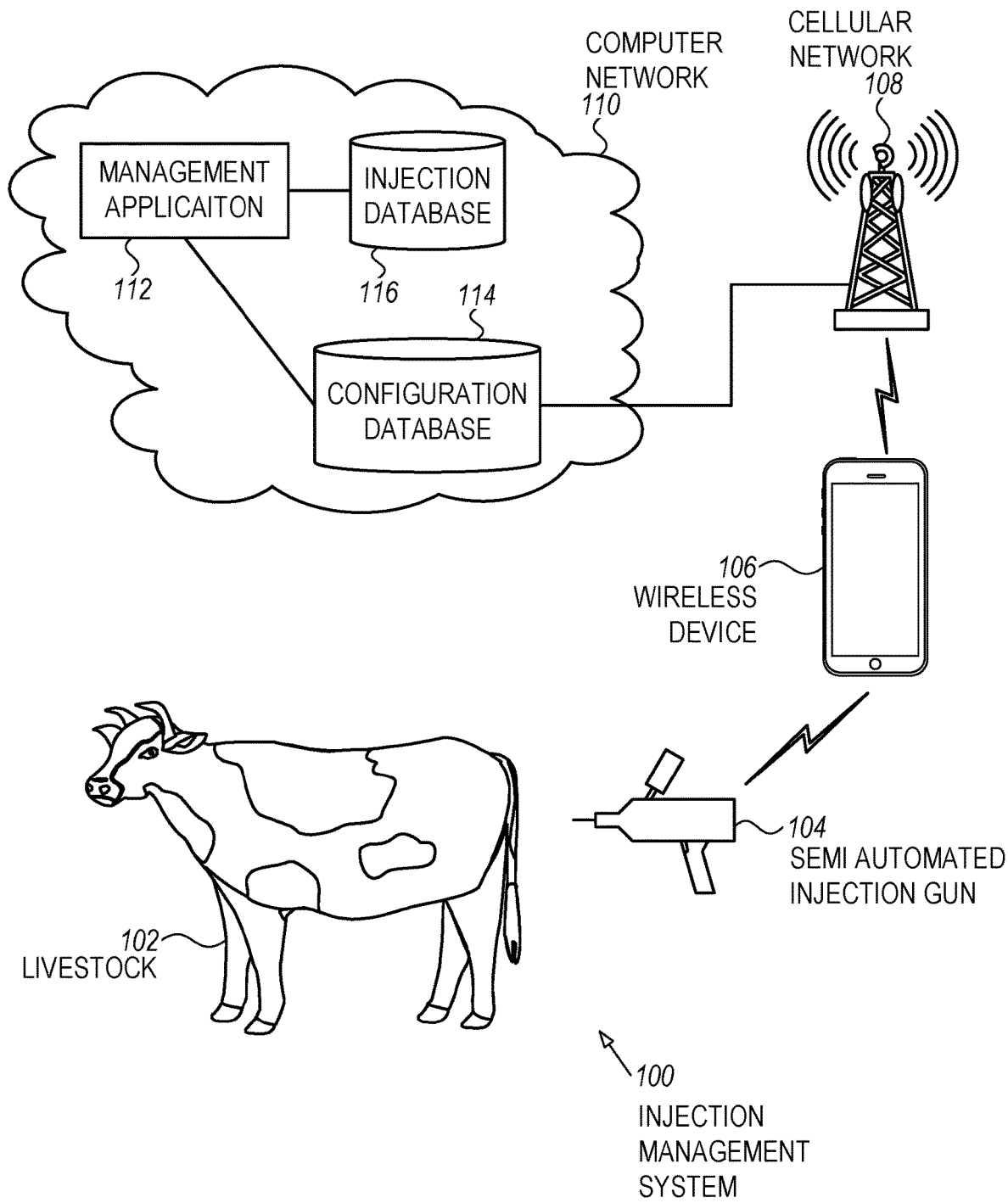
FIG. 1 is a diagram illustration of an embodiment showing a semi-automated dosing device in its ecosystem.

Animal Injection Dosing System with Fault Detection

An animal injection system may detect abnormalities with its operation and may administer a second dose to make up for a deficiency identified in a first dose. An incomplete or partial dose may be sensed during the operation of an injection, and that portion of the dose that may have been improperly administered may be calculated and the device configured to administer a makeup dose.

An animal injection system may monitor an injection process to determine whether an injection is properly administered. Error conditions may be identified when air may be present in a dose, the dose may be administered in the wrong location or depth into an animal, an injection needle may be removed during the injection process, a needleless injection process may be improperly given when the device is moved sideways or lifted during the injection process, or other error conditions.

When an incomplete dose is detected, the device may alert a user and may configure the device to administer a second dose to the animal. In some cases, the entire dose may be re-administered, while in other cases, a partial dose may be re-administered. When a partial dose is given, the device may calculate a makeup dose based on the portions of the original dose that was improperly administered.

For a needle-based injection system, a device may compare a position sensor on a syringe with a current sensor on a motor used to drive the syringe. For a given medicine or other substance being delivered, an expected amount of current may be compared against the linear motion of the syringe. The comparison signal may be analyzed to identify different scenarios, such as air within the syringe, whether a needle used for injection was properly placed in the animal, whether the needle was removed prior to completing the injection, whether the syringe was properly filled prior to injection, and other conditions.

A semi-automated device may have a syringe barrel that may be filled by retracting a plunger to draw a substance into the barrel. Once loaded with the substance, a trigger may cause the plunger to be advanced and the substance will be expelled from the syringe. For injected substances, the device may be fitted with a needle or an adapter may be configured for needleless delivery. Other substances may be delivered by pour-on, nasally, or orally, where the device may be fitted with a tube or nozzle.

The syringe plunger may be driven by an electric motor, both in the retraction and extension stroke. During retraction, medicines or substances may be drawn into the syringe barrel through a feeder passage, and during extension, the substances may be expelled through a needle, tube, or other expulsion conduit. Both the feeder passage and expulsion conduit may be fitted with check valves. The check valve on the feeder passage may prevent substance in the syringe barrel from being forced out through the feeder passage during the extension stroke. Similarly, the check valve on the expulsion conduit may prevent air from entering the syringe barrel during the retraction stroke.

Some versions of the device may use a rack and pinion mechanism to extend and retract the syringe plunger. The rack portion may be attached to the plunger, and the pinion may be operated by an electric motor. The rack portion may be attached to a position sensor, which may detect the linear motion travelled by the plunger. The electric motor may have a sensor to detects the motor's current draw. Other systems may use other mechanisms to drive a syringe and plunger, such as a chain and pulley mechanism, linear motors, or other mechanism.

A controller for the device may compare the linear motion of the syringe plunger with the current draw of the motor. By comparing the two signals, different conditions may be sensed during operation.

In normal operation, the device may retract the plunger to draw in the medicine or other substance into the syringe barrel. When a user positions the device ready for dosing, such as inserting the needle into the animal or arranging the oral drenching tube, the user may activate a trigger, which will cause the plunger to be extended to deliver the appropriate dose.

The motor may activate to deliver the dose and may advance the plunger forward until a measured dose is administered. In many cases, the syringe may be larger than a dose, and the motor may stop before fully emptying the syringe. In many cases, the weight or other characteristic of the animal may be used by the device controller to calculate an intended dose for that specific animal.

When a dose is smaller than the size of the syringe, the controller may calculate the size of the dose. In some cases, the dose from animal to animal may be identical, but in other systems, weight or other characteristics of the animal may vary the dose for each animal.

During the extension stroke when the substance is administered to an animal, the controller may monitor the linear motion of the plunger. The sensing of linear motion may have two uses: one may be to detect a predefined stop point to limit the dosage, and two may be to compare the linear motion to the current draw of the motor.

For normal operation, the viscosity of the medicine or other substance along with the orifice size of a needle or other delivery mechanism may determine how much force would be expected to be applied to the plunger to inject at a given rate. The force applied to the plunger may be directly proportional to the current draw of the motor per the distance travelled. When a dose is given within the normal range of force applied, the dose may be considered successfully administered.

When the measured force changes during delivery, a problem may be detected. When the force jumps from high resistance to low resistance, an air bubble may be assumed to be at the end of the chamber. In some cases, an air bubble may cause the force to be very low at the beginning then jump to the normal rage. Such an air bubble may be at the exhaust or needle end of the syringe.

One common condition may be when a user removes an injection needle too soon during an injection. This may occur when a user inserts a needle into an animal, activates the trigger, and the injection process begins. During the injection process, an animal may jump or move, causing the needle to come out of the animal while the plunger is advancing. Sometimes, this situation may occur when the user inadvertently removes the injection needle without recognizing that the injection has not yet completed.

In such a situation, the device may sense that the force applied to the syringe may be in the normal range but then the force may change to be much less. At the point that the force changes, the controller may record the approximate dosage actually administered. The controller may alert the user that the dose has not finished and may calculate a second dose, where the second dose may be the approximate amount remaining from the first dose.

Other problematic situations may occur when a dose may be administered without an animal, where the dosage may be shot into the air or on the ground. Such a situation may occur when a user inadvertently presses a trigger to fire the dosing device.

Still another situation may occur when the dosage was administered in the wrong portion of the animal. Some medicines may be designed to be administered intramuscularly, while others may be intended to be delivered into fat, subcutaneously, or into some other portion of the animal's body.

The resistance of the animal's tissue to an injection may be used as a signal to determine which layer of the animal's body received the injection. The signal may be compared to that of the expected layer of the animal's body and used to verify proper administration or to signal an error condition.

Some medicines or other substances may be administered in doses larger than the capacity of the syringe. In such cases, a complete dose may be administered in two, three, or more separate injections. Some medicines may be absorbed more readily when several smaller doses are administered rather than one larger dose.

In such a situation, the device may alert the user that there will be a set number of injections, and for example, the number may be three doses. The controller may indicate that the first dose is ready, when the user may place a needle in a first injection point and pull the trigger. After a successful injection, the device may re-load the syringe with more medicine, and the controller may indicate the second injection is ready. After inserting the needle in the second injection point and pulling the trigger, the device may administer the second dose. The third dose may follow the same procedure.

If one of the doses in a multi-dose sequence is detected to be incomplete, the controller may recalculate the next dose or doses to administer. In the case where an additional dose may be added because one or more of the previous doses in the multi-dose sequence was incomplete, the controller may notify the user and instruct the user to administer an additional dose.

With each dose, the controller may keep a record of the administered dose. In many cases, the identity of an animal being treated may be gathered, such as from an RFID tag, embedded chip, barcode, or other automated input. Some systems may have a manual input mechanism. A record of the actual dosage administered may be logged in a database. Such a database may be in the device controller or some other device.

For needleless injection devices, a sensor may be used to detect contact between the device and an animal's skin. The sensor may be a presence sensor or a force sensor, which may sense that the device remains in contact with the animal's skin during the injection process. Some systems may have a sensor that may detect lateral movement or sliding of the device across the surface of the animal's skin. During the injection sequence, a controller may monitor the sensor or sensors to determine whether proper contact and lack of movement was observed. If movement or lack of adequate pressure or contact were observed, the device may identify an improper injection and may configure itself to administer a makeup dose.

Throughout this specification and claims, the term "semi-automated dosing device" is used as a synonym for "dosing device" or, sometimes, "device" and refers to a device that applies doses to an animal with an inherent controller that can detect errors during dosing.

Throughout this specification, like reference numbers signify the same elements throughout the description of the figures.

In the specification and claims, references to "a processor" include multiple processors. In some cases, a process that may be performed by "a processor" may be actually performed by multiple processors on the same device or on different devices. For the purposes of this specification and claims, any reference to "a processor" shall include multiple processors, which may be on the same device or different devices, unless expressly specified otherwise.

When elements are referred to as being "connected" or "coupled," the elements can be directly connected or coupled together or one or more intervening elements may also be present. In contrast, when elements are referred to as being "directly connected" or "directly coupled," there are no intervening elements present.

The subject matter may be embodied as devices, systems, methods, and/or computer program products. Accordingly, some or all of the subject matter may be embodied in hardware and/or in software (including firmware, resident software, micro-code, state machines, gate arrays, etc.) Furthermore, the subject matter may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. By way of example, and not limitation, computer readable media may comprise computer storage media and communication media.

Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can accessed by an instruction execution system. Note that the computer-usable or computer-readable medium could be paper or another suitable medium upon which the program is printed, as the program can be electronically captured, via, for instance, optical scanning of the paper or other medium, then compiled, interpreted, of otherwise processed in a suitable manner, if necessary, and then stored in a computer memory.

When the subject matter is embodied in the general context of computer-executable instructions, the embodiment may comprise program modules, executed by one or more systems, computers, or other devices. Generally, program modules include routines, programs, objects, components, data structures, etc. that perform particular tasks or implement particular abstract data types. Typically, the functionality of the program modules may be combined or distributed as desired in various embodiments.

FIG. 1 is a diagram illustration of an example embodiment 100 showing an injection management system for livestock. Embodiment 100 may be one example of the various components that may administer and track the application of substances to livestock. In a typical use case, animals may be injected with vitamins, vaccines, or other medicinal substances. The system may validate that the doses were administered correctly and may keep a record of the dosing for various uses.

The system may identify whether or not a dose was properly administered at the point of administration. For example, a farmhand on a ranch may administer injections to livestock 102. With each injection, a device 104 may verify that the dose was properly administered. When a dose was improperly administered, the device 104 may indicate to the operator, in this case, the farmhand, to re-administer a dose. The device 104 may configure itself for a makeup dose for the animal, and indicate to the operator to re-administer.

The device 104 may keep electronic records of each animal and dose. In many cases, the device 104 may use RFID, barcode, or other electronic communication to identify a specific animal or groups of animals, and add an electronic record of the dosing for the animals.

The device 104 may communicate with a wireless device 106, which may transmit the records over a cellular network 108 to a computer network 110.

In this example, a wireless device 106 may be a cellular telephone or other device that may be brought into the field. In some use cases, especially where cellular connections may not be available, the wireless device 106 may gather the electronic records from the device 104 and store the records. Upon connection to a cellular network 108 at a later time, the wireless device 106 may transmit the records.

The wireless device 106 may be used to program or configure the dosing device 104. For example, the dosing parameters for a group of animals may be configured using a user interface on the wireless device 106. Once the dosing parameters are properly configured, the settings may be transmitted to the administration device 104. In many systems, the administration device 104 may have a limited user interface but a wireless device 106 may have a larger, more easily accessible user interface. Such systems may be designed so that more complex configuration and monitoring tasks may be performed on the wireless device 106 rather than the administration device 104.

The administration device 104 may have various user interface components. In some cases, the administration device 104 may have a digital display, where administrative and configuration functions may be performed, as well as monitoring and performance recording may be displayed.

The administration device 104 may have a simplified user interface that may be used during the routine of administering substances to animals. Such an interface may consist of a colored light or set of lights that may display different states of the device 104. The states may include ready to administer, successful administration, unsuccessful administration, redosing previous animal, or other statuses of the device. In many cases, such a light or set of lights may be the primary user interface that an operator may use while actively administering medicines in the field.

The dosing data may be transmitted to a computer network 110, where a management application 112 may manage and store configuration information in a configuration database 114 as well as store dosing information in an injection database 116. The management application 112 may perform various administrative functions, such as veterinary functions, production monitoring, tracking and provenance monitoring, and other functions.

The use cases for the system of embodiment 100 may include immunizing herds or flocks against specific diseases. A dosing regimen may be designed by a veterinarian to immunize a herd by injecting 90% of the population. The device 104 may be configured to verify that each dose was properly administered and to record the doses. An immunization contractor may use the device 104 to administer the doses and record their doses, thereby verifying that the contractor has successfully completed their contract. A production manager may use the same information to insure their herd against a disease outbreak as the livestock matures. Finally, consumers may validate the provenance of their food through a record of an animal's history, which may include the dosing information.

Figure 2:
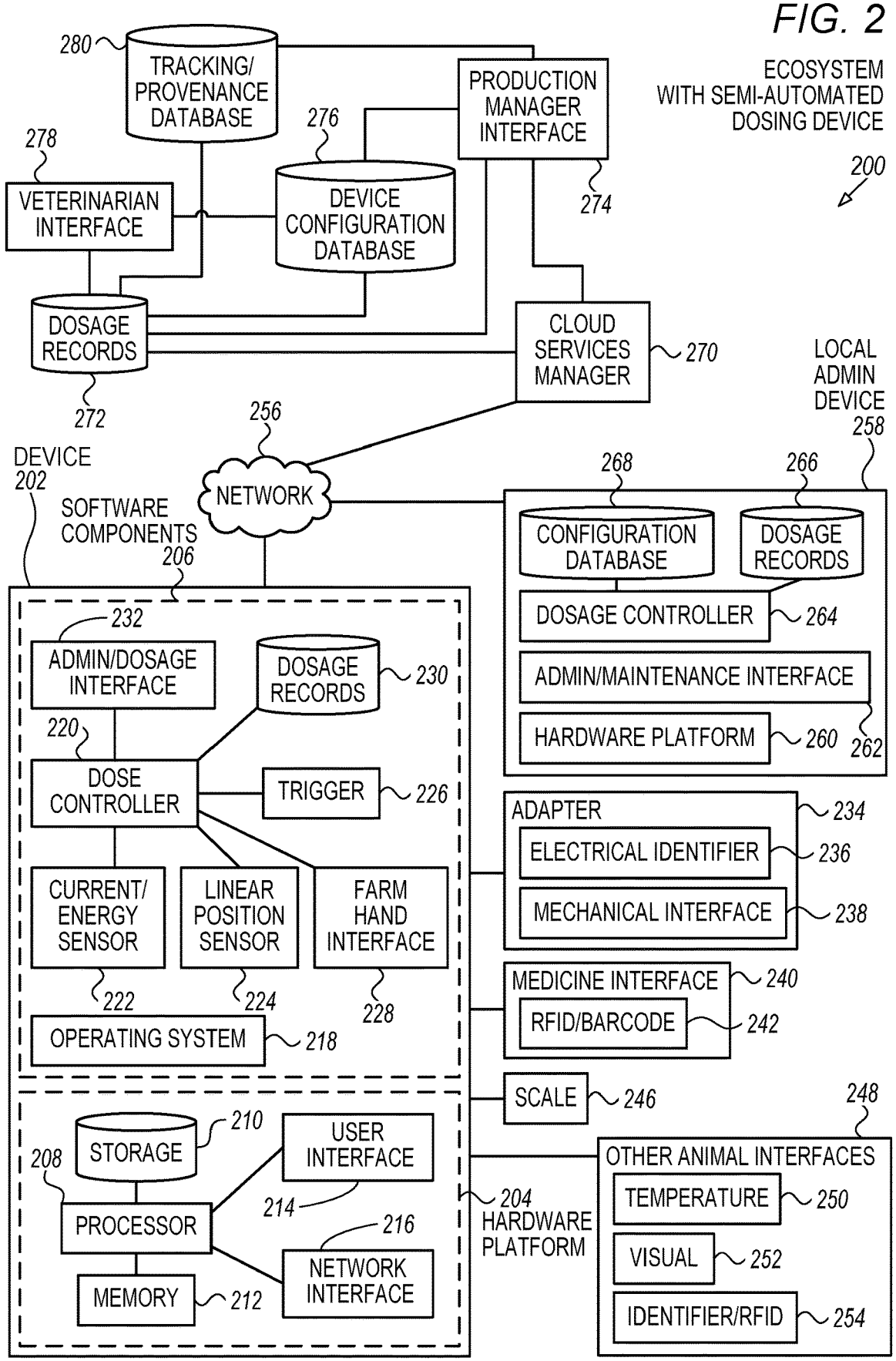
FIG. 2 is a diagram illustration of an embodiment showing a schematic or functional representation of a network with a semi-automated dosing device.

The diagram of FIG. 2 illustrates functional components of a system. In some cases, the component may be a hardware component, a software component, or a combination of hardware and software. Some of the components may be application level software, while other components may be execution environment level components. In some cases, the connection of one component to another may be a close connection where two or more components are operating on a single hardware platform. In other cases, the connections may be made over network connections spanning long distances. Each embodiment may use different hardware, software, and interconnection architectures to achieve the functions described.

Embodiment 200 illustrates a device 202 that may have a hardware platform 204 and various software components. The device 202 as illustrated represents a conventional computing device, although other embodiments may have different configurations, architectures, or components.

The hardware platform 204 may include a processor 208, random access memory 210, and nonvolatile storage 212. The hardware platform 204 may also include a user interface 214 and network interface 216.

The random access memory 210 may be storage that contains data objects and executable code that can be quickly accessed by the processors 208. In many embodiments, the random access memory 210 may have a high-speed bus connecting the memory 210 to the processors 208.

The nonvolatile storage 212 may be storage that persists after the device 202 is shut down. The nonvolatile storage 212 may be any type of storage device, including hard disk, solid state memory devices, magnetic tape, optical storage, or other type of storage. The nonvolatile storage 212 may be read only or read/write capable. In some embodiments, the nonvolatile storage 212 may be cloud based, network storage, or other storage that may be accessed over a network connection.

The user interface 214 may be any type of hardware capable of displaying output and receiving input from a user. In many cases, the output display may be a graphical display monitor, although output devices may include lights and other visual output, audio output, kinetic actuator output, as well as other output devices. Conventional input devices may include keyboards and pointing devices such as a mouse, stylus, trackball, or other pointing device. Other input devices may include various sensors, including biometric input devices, audio and video input devices, and other sensors.

The network interface 216 may be any type of connection to another computer. In many embodiments, the network interface 216 may be a wired Ethernet connection. Other embodiments may include wired or wireless connections over various communication protocols.

The software components 206 may include an operating system 218 on which various software components and services may operate.

A dose controller 220 may be a routine that controls the administration of a dose by monitoring a current or energy sensor 222 and a linear position sensor 224 while a syringe plunger is advanced through a syringe body. The energy sensor 222 and linear position sensor 224 are one mechanism to measure force exerted while a syringe moves.

By monitoring the force exerted while a syringe plunger moves within a syringe body, the measured force may be compared to an expected force to determine whether a dose was administered as expected or whether an error may have occurred. Further, the type of error may be identified by analysis of the force signal.

One error that may occur is that air may have been captured in the syringe body. In general, air is highly compressible while liquid doses may not be. When air is present, the force applied to a syringe body may be much different than when a syringe body contains no air. This difference can be identified to detect that air is present.

Further, the amount of air present may be calculated by signal analysis. When the amount of air can be calculated, a make up dose may be calculated. For example, a dose that may be administered with a syringe that contains 60% medicine and 40% air may have a second, makeup dose calculated to be 40% of the original dose. When the dose controller 220 detects such an incomplete dose, an alert may be made to an operator, who may then administer the makeup dose to the animal.

Another type of error may occur when a dose may be administered without an animal present. Such a situation may occur when a trigger 226 may be activated prior to inserting an injection needle into an animal. When the device 202 activates the syringe and no animal is present, the force detected by a current or energy sensor 222 and a linear position sensor 224 may give a much different signal than expected. Such a signal may also be different from a signal when air is present in the syringe, and thereby the device 202 may be capable of isolating such an error.

Yet another type of error may occur when an injection location was improper. Some medicines are intended to be delivered intramuscularly, while others are to be delivered subcutaneously, in the animal's fatty tissue, or some other location. Each of these various locations may provide a different level of resistance during injection, and by analyzing the force signal during injection, the dose controller 220 may be able to differentiate between the intended and an improper location for the dose.

In some cases, an error may occur because the position of an injection needle may change during dosing. An animal may jerk or move, or an operator may withdraw the needle while an injection occurs. In such a case, an injection may begin properly, but may change during the injection sequence. By monitoring the force signal, such changes may be identified and an error condition may be isolated.

Such an error condition may be identified and communicated to the device operator. The communication may alert the operator that the injection was not in the right location or that the injection was incomplete. Such feedback may help the operator correctly place the needle for future doses.

In some such situations, the dose controller 220 may determine that redosing may be appropriate, while in other situations, the improper dose may be logged but may not be sufficiently bad to warrant redosing.

The force exerted on a syringe plunger within a syringe body may be monitored in many different manners. In embodiment 200, a current or energy sensor 222 may be coupled with a linear position sensor 224. A current or energy sensor 222 may measure current draw to an electric motor, while the linear position sensor 224 may measure physical movement. The combination of the two measurements may yield force applied to the syringe.

Other mechanisms may be used to generate similar signals, including force sensors placed on the syringe mechanism, pressure sensors within the syringe body, or other sensors and locations. Such sensors may generate similar signals that may be generated using the energy sensor 222 and linear position sensor 224.

The dose controller 220 may communicate with a human operator using a farm hand interface 228. The farm hand interface 228 may be the interface through which an operator may be given the status of the device 202, as well as alerts to administer doses, re-administer makeup doses, success or failure of doses, and other status or alerts. In many cases, the farm hand interface 228 may not allow the operator to make changes to the dosing or perform other administrative changes to the device. A typical user interface may be as simple as a single light, a set of lights, multicolored lights, or some other simple signal.

Some devices 202 may include a graphical, text, or other user interface. Such interfaces may display a count of doses administered, text based or graphical representations of the success or failure of the doses, and other information.

With each operation of the device 202, records may be written to the dosage records 230. The dosage records 230 may be a local repository of doses. In many use cases, the device 202 may store dose information, then may transmit that information to another device at some later point. In many use scenarios, doses may be administered on a ranch or some other rural location that may be many miles from a connection to a cellular or other communications network.

An administrative or dosage interface 232 may be a mechanism by which the device 202 may be configured and managed. Through such an interface, the device 202 may be configured, updated, and managed. In many cases, the interface 232 may have the capability of configuring the dosage information to be applied to animals. In some embodiments, such functions may be available to managers or veterinarians, and in such embodiments, the farm hand operators may not be able to adjust dosage or reconfigure the device 202.

The device 202 may have various adapters 234. Different adapters 234 may have needle injection devices, needleless injection, intranasal delivery, oral or pour-on delivery, or other methods of medicine delivery. Such designs may allow a standardized "gun" device 202 to be reconfigured for different use cases. Each adapter 234 may have an electrical identifier 236 as well as a mechanical interface 238.

An electrical identifier 236 may be an RFID, barcode, chip, or other electrically-readable identifier that the device 202 may query to determine which adapter 234 has been installed. In many cases, a dosage may be defined to be applied in a specific manner, and such a dosage definition may include an adapter definition for that dosage. During normal operation, the dose controller 220 may compare the required adapter definition for the dose with the adapter's electrical identifier 236 to validate that the proper adapter is present.

The mechanical interface 238 may be a mechanical connection between the device 202 and the adapter 234. The mechanical interface 238 may vary from one design to the next, and may include the applicator portion that may come in contact with an animal. In an example of needle-based injections, the adapter 234 may be quickly replaceable so that needles may be replaced after so many uses.

A medicine interface 240 may include an RFID or barcode identifier 242. The medicine interface 240 may be one way that the medicine may be logged by the dose controller 220 in the dosage records 230. In many cases, a medicine container may have radio frequency identifiers (RFID), barcode, or other machine-readable identifier. The device 202 may capture the identifier and compare the actual identifier with the medicine identifier intended for the dosing to be administered.

Some systems may operate with a scale 246 or other animal interfaces 248. Such interfaces may include temperature measurements 250, visual capture devices 252, animal identifiers 254, or other inputs. Parameters collected by these devices may be used to calculate dosing as well as record keeping for the dosing.

Inputs such as animal weight gathered from a scale 246 or animal temperature 250 may be used to calculate dosing for a specific animal. In many cases, dosing may be defined as a function or weight, age, temperature, or other factor. The dose controller 220 may be programmed to calculate a dose using such factors for each animal, and a record of the weight or other factor may be stored with the dosage in the dosage records 230.

The device 202 may be connected to a network 256 to various other devices.

One such device may be a local administrative device 258. The local administrative device 258 may operate on a hardware platform 260 and may have an administrative or maintenance interface 262 as well as a dosage controller 264.

In many use cases, the local administrative device 258 may be used to program and manage the device 202, and may store dosage records 266 gathered from the device's dosage records 230 for later communication to other computer systems. In many systems, a single local administrative device 258 may be used to manage several devices 202 in the field.

The local administrative device 258 may have a dosage controller 264 which may operate with a configuration database 268 to create and manage doses. The configuration database 268 may have configuration information and options available for the device 202, including typical dosing information for specific medicines and other information. Such a database may be used by someone in the field to configure the device 202.

A cloud services manager 270 may be a service operable in a cloud architecture that may provide management, record keeping, and configuration services for the device 202 and local administrative device 258.

A database of dosage records 272 may be gathered from the device 202 or local administrative device 258. Such a database may be accessed by a veterinarian interface 278, a production manager interface 274, or other interface.

A production manager interface 274 may be used by a supervisor of a livestock operation to track the animals under their care. The production manager interface 274 may allow such a supervisor to schedule doses, monitor when the doses were administered, and capture other information regarding the livestock.

A veterinarian interface 278 may be used by a veterinarian to review dosage administration and other parameters regarding the health and well being of the livestock.

Both the production manager interface 274 and veterinarian interface 278 may interact with a device configuration database 276 to create dosage regimes for livestock. The dosage information and device configurations may be set and transmitted to the local administrative device 258 or device 202. Once transmitted to the device 202, a farm hand may administer the doses to the animals.

Figure 3:
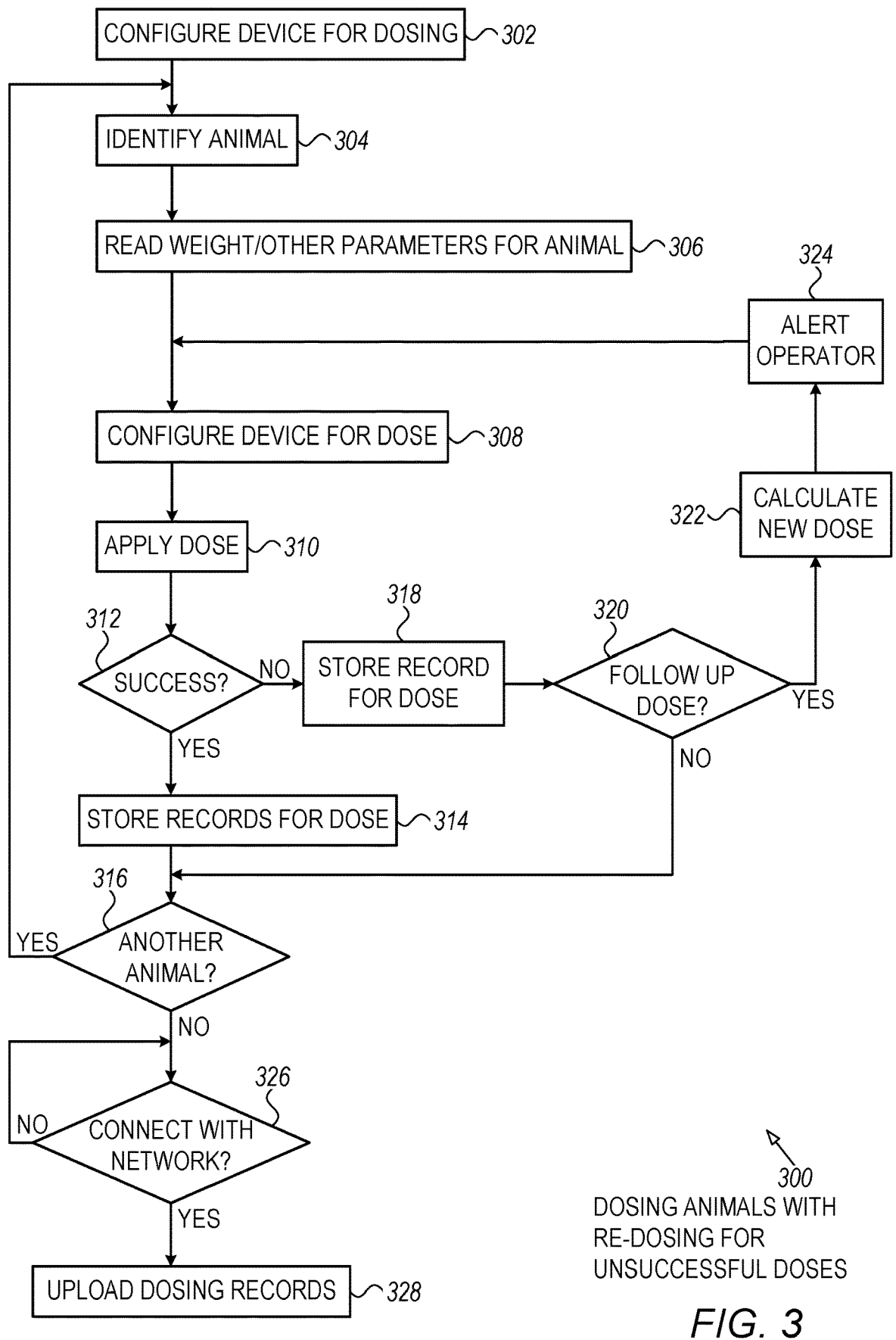
FIG. 3 is a flowchart illustration of an embodiment showing a method for dosing animals with re-dosing in case of an error.

FIG. 3 is a flowchart illustration of an embodiment 300 showing a method for dosing animals with a re-dosing process for unsuccessful doses. The operations of embodiment 300 show one workflow of how a semi-automated dosage system might be deployed to administer medicines, vaccines, or other substances to livestock.

Other embodiments may use different sequencing, additional or fewer steps, and different nomenclature or terminology to accomplish similar functions. In some embodiments, various operations or set of operations may be performed in parallel with other operations, either in a synchronous or asynchronous manner. The steps selected here were chosen to illustrate some principles of operations in a simplified form.

A device may be configured in block 302. The configuration may include receiving parameters defining how a dose will be administered, such as dosage size, the configuration of the dosing device, adapters to be used, any formulas used to calculate dosing, and the like. The configuration may also include an expected force-related signal that the application device may experience during normal operation.

The force-related signal may be defined in a manner such that a dosing device may be able to determine whether a dose was properly administered as well as any error conditions. One such error condition may be to calculate how much of a dose was properly administered such that a makeup dose may be calculated and administered.

An animal may be identified in block 304. In a typical use case, an animal's RFID tag may be read, for example. The animal's weight or other parameters may be gathered in block 306.

A dosage may be calculated in block 308 and the device may be configured for the dose in block 308. The dose may be applied in block 310.

If the dose was a success in block 312, the record of the dose may be stored in block 314, and if another animal is to be dosed in block 316, the process may return to block 304.

If the dose was not a success in block 312, the improper dose may be recorded in block 318 and a determination may be made whether a follow up or makeup dose may be made in block 320. If a makeup dose is to be performed in block 320, the new dose may be calculated in block 322. The operator may be notified in block 324, and the process may return to block 308 to configure and administer the makeup dose. The process may loop back again if the second dose was not proper as well.

After all animals have been processed in block 316, a waiting loop may occur in block 326 until a connection is made with a network. Once the network connection is established in block 326, the dosing records may be uploaded in block 328.

Figure 4:
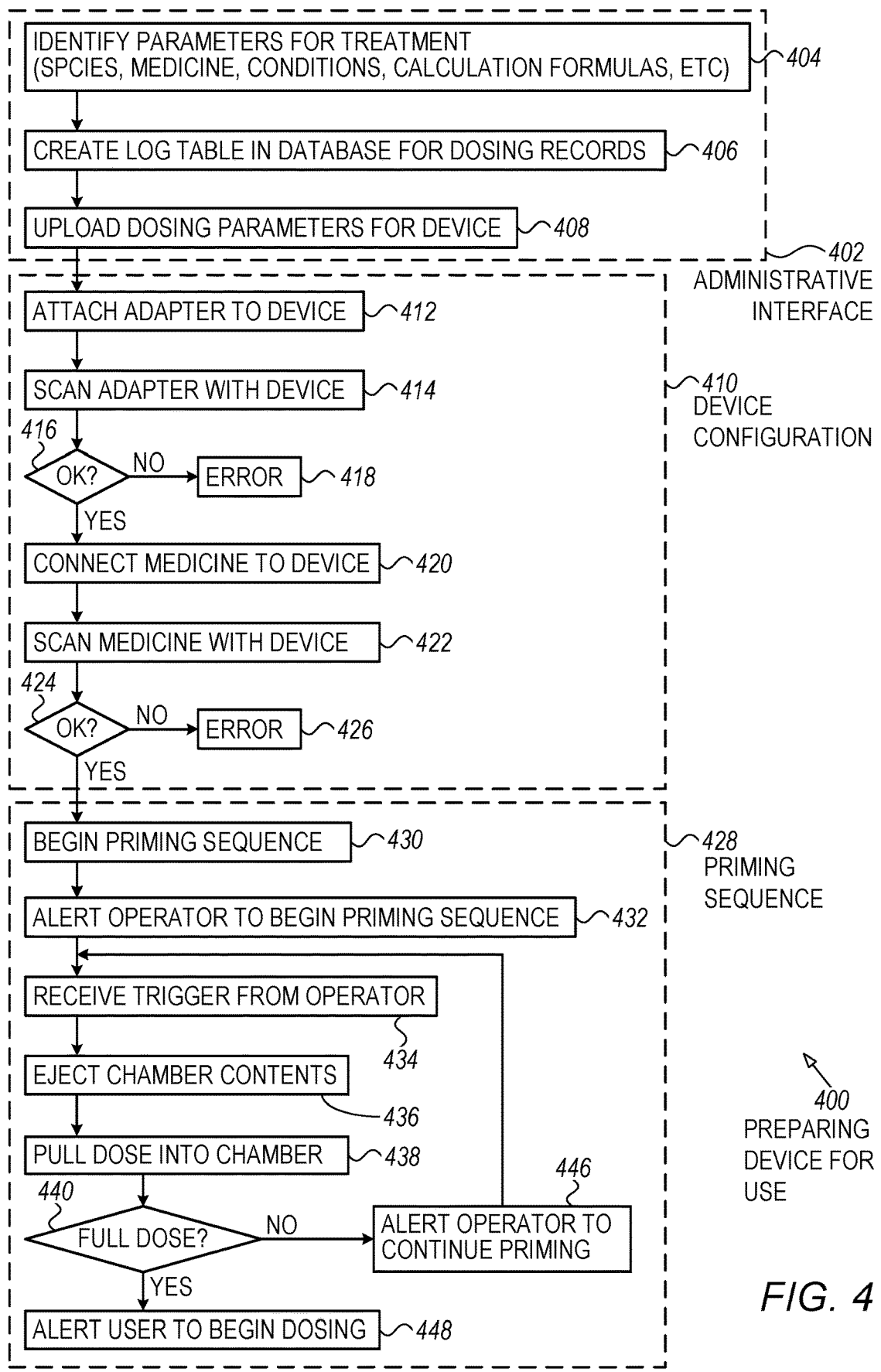
FIG. 4 is a flowchart illustration of an embodiment showing a method for preparing a dosing device for use.

FIG. 4 is a flowchart illustration of an embodiment 400 showing a method for preparing a semi-automated dosing device for use. The operations of embodiment 300 show one workflow for deploying a dosing regimen, configuring a device, and going through a priming sequence. The workflow of embodiment 400 illustrate merely one sequence that may be deployed to get a device operational for dosing.

Other embodiments may use different sequencing, additional or fewer steps, and different nomenclature or terminology to accomplish similar functions. In some embodiments, various operations or set of operations may be performed in parallel with other operations, either in a synchronous or asynchronous manner. The steps selected here were chosen to illustrate some principles of operations in a simplified form.

A set of functions may be performed by an administrative interface in block 402. The administrative functions may identify parameters for treating animals in block 404, creating a log table for the dosing records in block 406, and uploading the configuration parameters to the dosing device in block 408.

The parameters for treating animals in block 404 may include identifying the animals being treated. In many cases, the animals may be identified by species, herd location, and, when known, the individual animals for which treatment is prescribed.

The parameters may also include information about the medicine or other substance to be administered. The substance information may include the identifiers for the medicine as well as physical characteristics. One characteristic may be viscosity of the substance, and in some cases, a viscosity curve that gives viscosity as a function of temperature. Viscosity may affect the amount of force expected to be applied to a syringe to draw the substance into the syringe body and to expel the sub stance.

The parameters may include conditions under which the medicines may be administered. The conditions may include the environmental conditions, such as outdoor temperature range, but may also include the location within the animal where the substance may be delivered. Such a location may be intramuscular, into fatty tissue, subcutaneous, intranasal, orally, drenching on the surface of the animal, or some other location. Such location information may inform the expected resistance level that may be experienced by a force measurement taken during the injection process.

A device configuration block 410 may include the mechanical and electrical configuration of the device. An adapter may be mechanically attached in block 412 and scanned electrically in block 414 to determine the adapter's identification. If the wrong adapter is attached in block 416, an error may be flagged in block 418 and the operator alerted.

Providing that the adapter is correct in block 416, the medicine may be connected to the device in block 420 and scanned in block 422. Different devices may have different types of reservoirs of medicine or other substance to be injected. In some cases, a reservoir may be worn on an armband, slung around one or both shoulders, or otherwise connected to an application device through a hose or tube. If the medicine is incorrect in block 424, an error may be flagged in block 426 and an operator alerted. Once the appropriate adapter and medicine has been configured, the device may be ready for priming.

The priming sequence may be in block 428. The sequence may begin in block 430, and the operator may be alerted in block 432. The operator may activate a trigger in block 434, where the plunger may eject whatever is in the syringe body in block 436, then pull in a dose into the syringe body or chamber in block 438.

While pulling in the substance to the syringe body, a dose controller may monitor the force applied to the syringe plunger. The force may be measured, for example, through an energy or current sensor on an electric motor along with the linear motion measured for the syringe plunger's movement. When the force deviates from the expected force profile of a full chamber in block 440, the operator may be alerted in block 446, and the operator may again trigger the operation in block 434.

A priming operation may pump the syringe several times to load the syringe body with a full compliment of medicine. When initially configured, air may be present in the chamber, tubing, and other components. As the priming operation continues, the air may be removed and the lines and chamber filled with the substance to be injected. Once the system has been properly primed, an alert may be made to indicate to the operator that dosing may begin in block 448.

Figure 5:
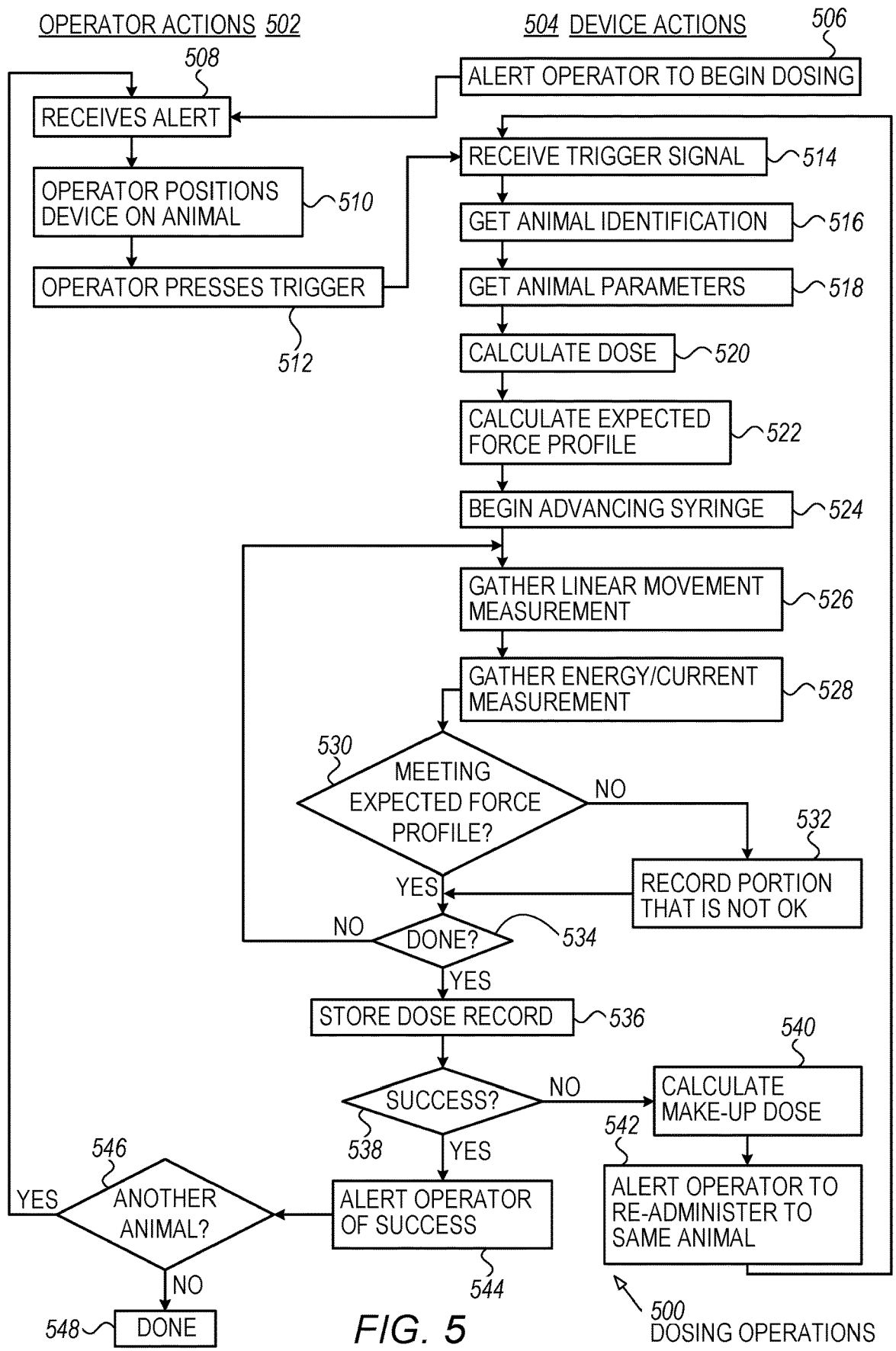
FIG. 5 is a flowchart illustration of an embodiment showing a method for dosing operations of a semi-automated dosing device.

FIG. 5 is a flowchart illustration of an embodiment 500 showing a method for dosing animals. The operations of embodiment 500 show operations performed by an operator 502 and a semi-automated dosing device 504.

Other embodiments may use different sequencing, additional or fewer steps, and different nomenclature or terminology to accomplish similar functions. In some embodiments, various operations or set of operations may be performed in parallel with other operations, either in a synchronous or asynchronous manner. The steps selected here were chosen to illustrate some principles of operations in a simplified form.

The device 504 may alert an operator to begin dosing in block 506. The operator 502 may receive the alert in block 508 and may position the device for dosing on the animal in block 510, then activate the device trigger in block 512.

The positioning operation of block 510 may be different for various ways of applying the substance to an animal. In a needle injection process, a needle may be inserted into the animal's body in the appropriate location, depth, and angle for the intended delivery. In a needleless injection, the needleless injection adapter may be pressed against the animal's body with the appropriate force. In an intranasal delivery, the application device may be inserted into an animal's nasal passage. In an oral delivery, the application device may be inserted into an animal's throat. In a pour on delivery, the application device may be placed on the animal's back to deliver to the animal's skin.

A trigger signal may be received in block 514 by the device 504. The animal identification may be scanned in block 516 and any parameters associated with the animal may be retrieved in block 518. The parameters may include, for example, the animal's weight.

The dosage may be calculated in block 520 and an expected force profile may be determined in block 522.

The syringe plunger may begin advancing in block 524 to deliver the substance to the animal. As the plunger advances, linear movement may be gathered from a linear movement sensor in block 526 and energy or current consumed may be gathered in block 528. Such measurements may occur in real time during the motion of the plunger.

If the measurements are not staying within an expected profile, the portion of the movement that is not OK is recorded in block 532. If the dosage has not completed, the process may return to block 526 to continue monitoring as the movement occurs. The monitoring and measurement may occur continually during the movement of the syringe plunger.

Once the syringe plunger has moved according to the dose in block 534, the dose record may be stored. If the dose was not a success in block 538, a make up dose may be calculated in block 540. The operator may be alerted in block 542, and the process may return to block 514 to receive another trigger signal and administer a makeup dose.

If the dose was a success in block 538, an alert may be given in block 544 that the dose was successful. If the operator 502 has additional animals to dose in block 546, the process may return to block 508. If not, the process may terminate in block 548.

Figure 6:
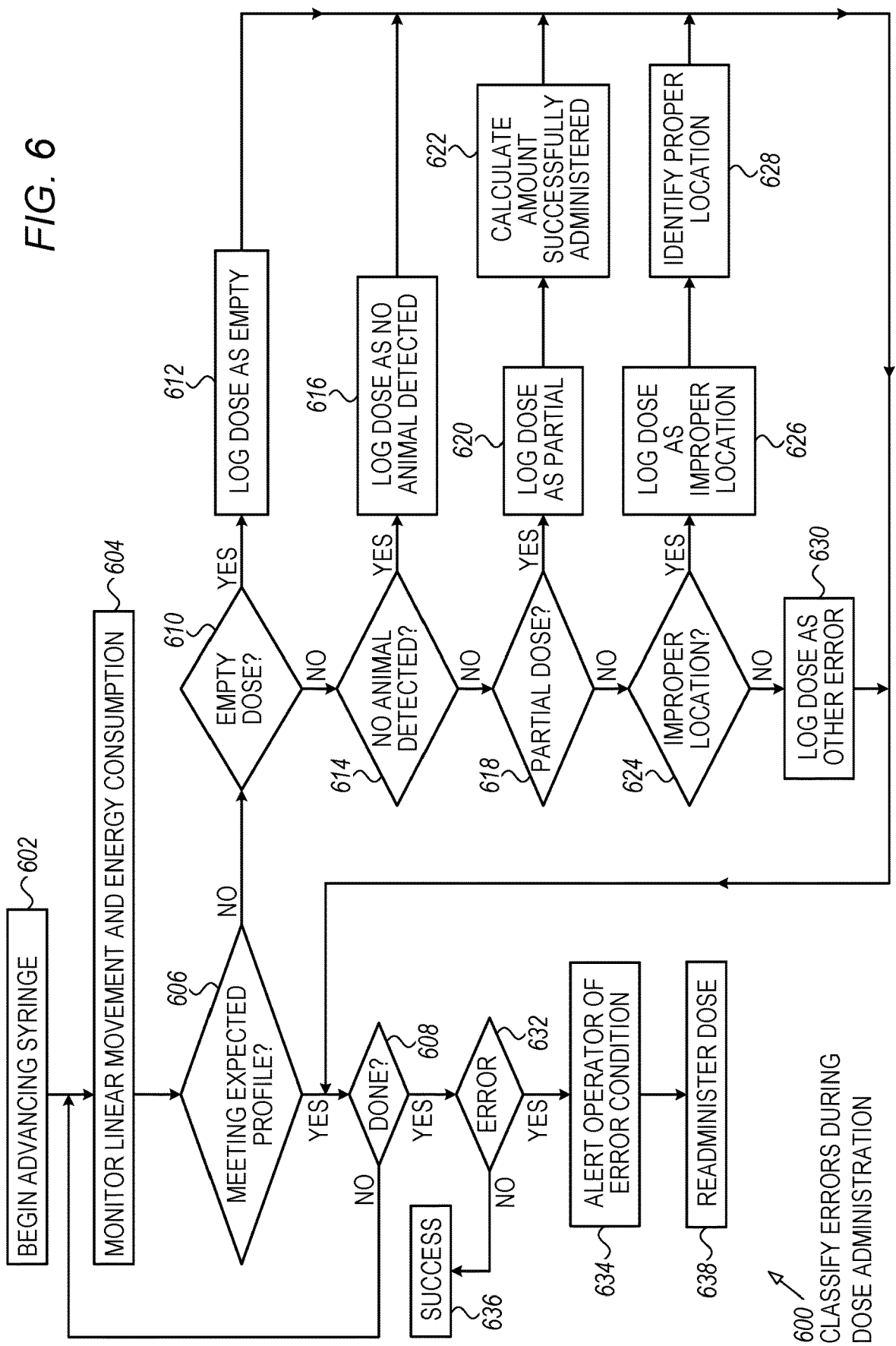
FIG. 6 is a flowchart illustration of an embodiment showing a method for classifying errors during a dosing cycle.

FIG. 6 is a flowchart illustration of an embodiment 600 showing a method for classifying error during dose administration using a semi-automated dosing device. The operations of embodiment 600 show one workflow of how a semi-automated dosage system might identify specific error conditions that may occur during dosing.

Other embodiments may use different sequencing, additional or fewer steps, and different nomenclature or terminology to accomplish similar functions. In some embodiments, various operations or set of operations may be performed in parallel with other operations, either in a synchronous or asynchronous manner. The steps selected here were chosen to illustrate some principles of operations in a simplified form.

Embodiment 600 illustrates several different error conditions that may be detected by analyzing force applied to a syringe plunger. These error conditions may be used to correct a detected problem by re-administering a dose.

Embodiment 600 begins at the stage where a syringe plunger is being advanced during a dosing event in block 602. During the movement, the linear movement and energy consumption may be monitored in block 604. In embodiments where a force sensor, internal pressure sensor, or another sensor that measures forces applied directly, such a sensor may be monitored in lieu of a separate linear motion sensor and current or energy consumption sensor.

If the forces being exerted are meeting the expected profile in block 606, and the dose has not completed in block 608, the process loops back to block 604.

If the forces being exerted are not meeting the expected profile in block 606, several different types of errors may be detected. In block 610, an empty dose may be detected. An empty dose may be a dose where the syringe may be filled with air and provides very little resistance while expelling the dose. Such a situation may be logged as an empty dose in block 612. In many cases, an empty dose may cause a priming operation to be performed, followed by a second attempt at dosing the animal.

A dose may be made with a full chamber of a syringe, yet the animal may not be present in block 614. Such a situation may happen when an operator presses the trigger to begin operation prior to positioning the device appropriately. In a needle-based injection, the needle may be inserted into the animal's body. In a needleless injection system, the injection point may be placed against the animal's body. In an intranasal delivery, the applicator may be placed in the animal's nose.

For some pour on or oral delivery systems, the animal may not create any detectable resistance, so such an error condition may not be sensed by a force sensor as described.

When a dose may be given in block 614 when no animal is present, the dose may be logged as no animal detected in block 616. In many cases, such an error may cause the device to configure itself to re-apply the same dose and may alert the operator to re-apply the dose to the same animal.

In some situations, the forces being exerted may indicate that a partial dose was applied. A partial dose may occur when an operator removes a needle or other applicator during the dosing process, which may happen, for example, when an animal moves during the process. Another cause of a partial dose may occur when the syringe may contain some air and some medicine. In such a case, a partial dose of medicine may be delivered.

When a dose was detected to be partial, the dose may be logged as such in block 620. A calculation may be performed in block 622 to determine how much of the dose was properly administered and how much was not. Such a calculation may be used to determine the size of a makeup dose.

A dose may be placed in an improper location in block 624. An improper location may be in the wrong portion of an animal. For example, a subcutaneous injection may be improperly placed in the animal's muscle or fat tissue. Another example may be an intramuscular injection that may be placed too shallow, such as in fatty tissue or subcutaneously.

An improper location may be detected when the resistance of particular portions of the animal's anatomy may be different enough that an analysis of force curves may identify improper location. When a dose may be identified as improperly located in block 624, the dose may be logged in block 626 and the proper or intended location may be identified in block 628. An alert may be sent to an operator so that the operator may correct future doses. In some situations, a dose may be re-administered.

If a deviation from the force profile may be detected in block 606 but not otherwise classified, the dose may be logged as having an unknown or other type of error in block 630.

Once an error has been detected, the process may return to block 608 and may continually monitor the remaining portion of the dose administration.

When the dose has completed in block 608, if an error has not occurred in block 632, a successful dose may be identified in block 636. If an error has occurred in block 632, the operator may be alerted in block 634 and, in some cases, the dose may be re-administered in block 638.

Figure 7:
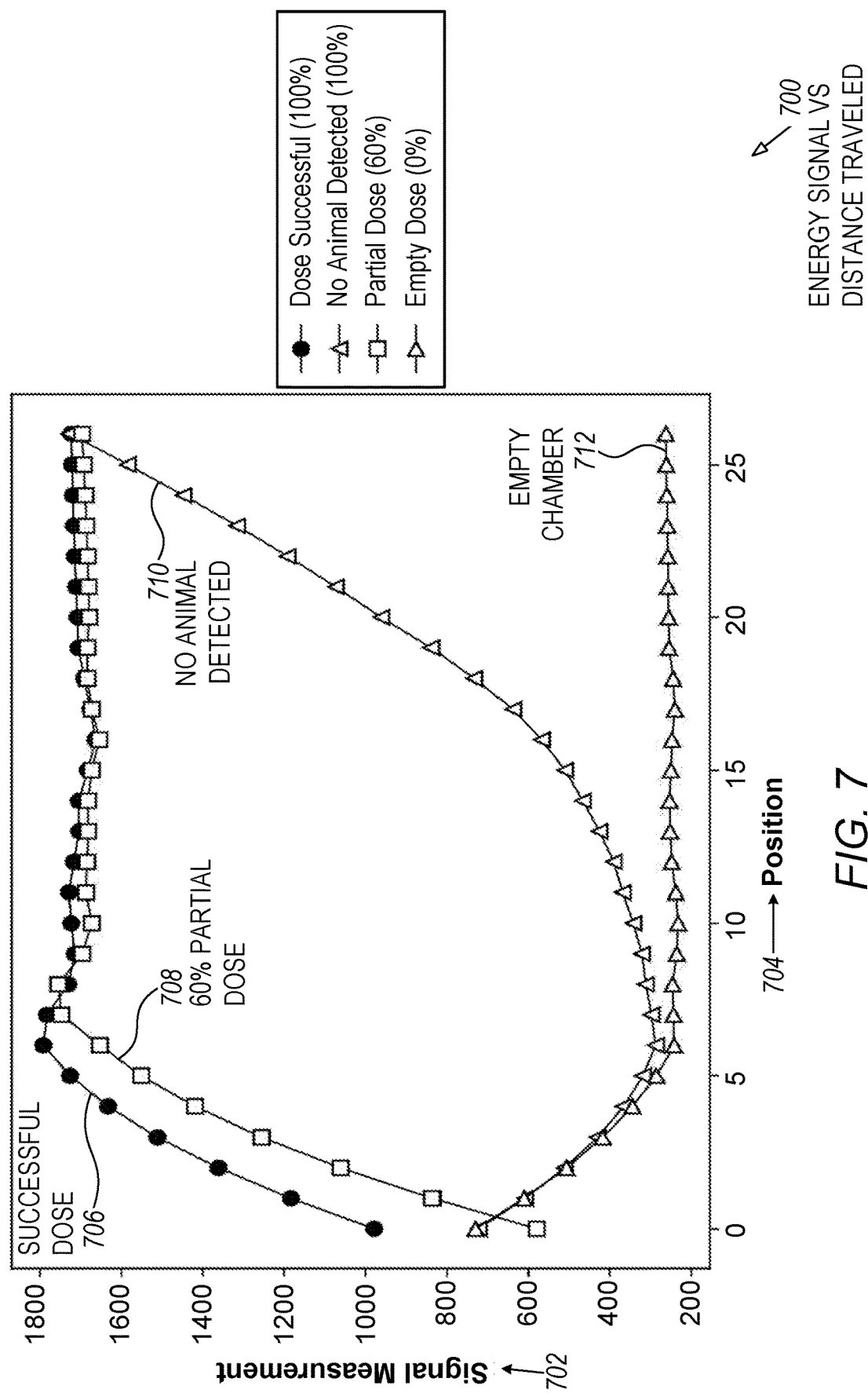
FIG. 7 is a dimensionless chart showing energy signal vs distance traveled curves for different dosing situations.

FIG. 7 is an illustration of an embodiment 700 showing several force curves. In embodiment 700, a dimensionless signal 702 is shown on the Y axis and dimensionless position is shown in the X axis. The curves illustrate measurements of current or energy consumed as a syringe plunger is driven forward to expel a medicine from an injection-type semi-automated dose administration device.

The curve 706 may be a successful dose, which the curve 708 may be a partial dose, where 40% of the chamber may have been filled with air. The successful dose shows a high rate of current draw initially, then continues at a high level during the dose administration. The curve showing a partially filled chamber is similar but offset. At the beginning of the partially filled curve 708, the initial force is lower than the fully filled dose curve 706, but once the air is compressed at the first measurement, the force curve 708 follows about the same shape as the fully filled curve 706.

The curves 710 and 712 show no animal detected in curve 710 and an instance of an empty chamber in curve 712. The no animal detected curve 710 may occur with a fully filled chamber, but since the animal may not be present and offers no resistance, the signal measurement drops initially. The signal measurement increases over time, as the resistance of the medicine flowing through the needle increases.

In contrast, the curve 712 shows an empty chamber. This curve starts out similar to the no animal detected curve 710, but continues with very little resistance because the lack of a viscous fluid to provide resistance.

The curves of embodiment 700 illustrate that analysis of force curves or current/energy vs linear movement may be used to isolate different error conditions that may occur during use of a semi-automated dosing device. When an unsuccessful dose may be identified, the dose may be logged and an appropriate remediation may be applied. In some cases, the entire does may be re-administered. In cases where the dose may be partially administered, a makeup dose may be calculated and re-administered.

Figure 8:
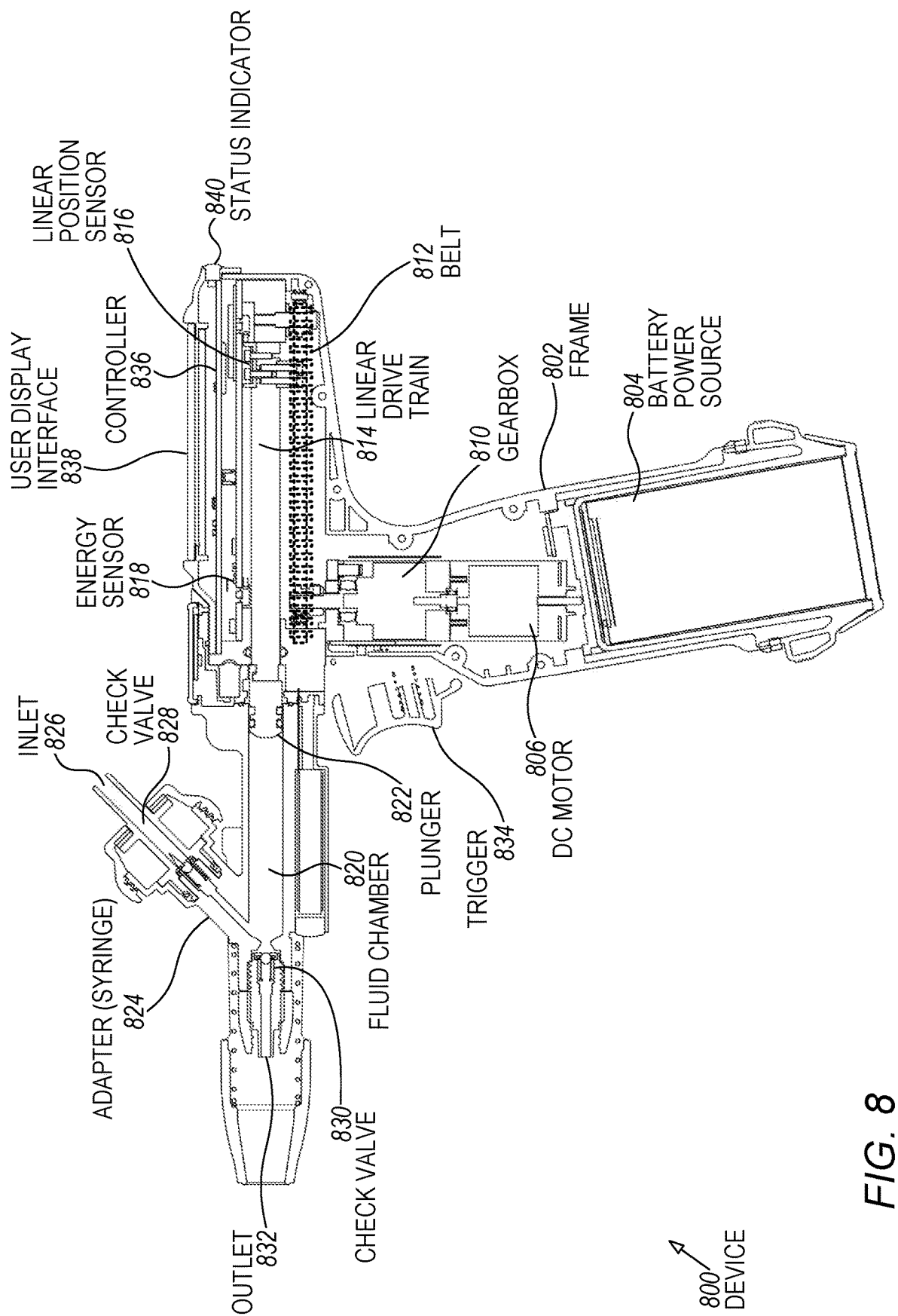
FIG. 8 is a cutaway illustration of an embodiment showing a semi-automated dosing device.

FIG. 8 is a cut-away illustration of an embodiment 800 showing a semi-automated dosing device.

The device 800 has a frame 802, power source 804, and a DC motor 806.

The DC motor 806 may drive a gearbox 810 and a belt 812, which is part of a linear drivetrain 814 which drives the syringe plunger 822. A linear position sensor 816 and energy or current sensor 818 may combine to determine the force being applied to the plunger 822 as the plunger 822 travels through the fluid chamber 820.

An adapter 824 may be illustrated as a needle-based injection system. Medicine or other substance may be introduced through an inlet 826. When the plunger 822 is moved to the right (as illustrated), a vacuum may be created inside the fluid chamber 820, drawing the substance past a check valve 828 and filling the fluid chamber 820, also known as a syringe body. During the fill process, a check valve 830 may be positioned so that air is not drawn into the fluid chamber 820 from the needle or administration end of the device.

When the plunger 822 is moved to the left (as illustrated), the check valve 828 from the inlet feed may be pushed closed and the check valve 830 at the administration end may open, allowing the substance to exit the device through the outlet 832.

The device 800 may be outfitted with a controller 836, which may be in electrical contact with the various sensors as well as a user display 838 mounted on the top of the device. Further, a status indicator 840 may be a light, multicolored light, or set of lights that may give a quick visual status of the device during operation.

Figure 9:
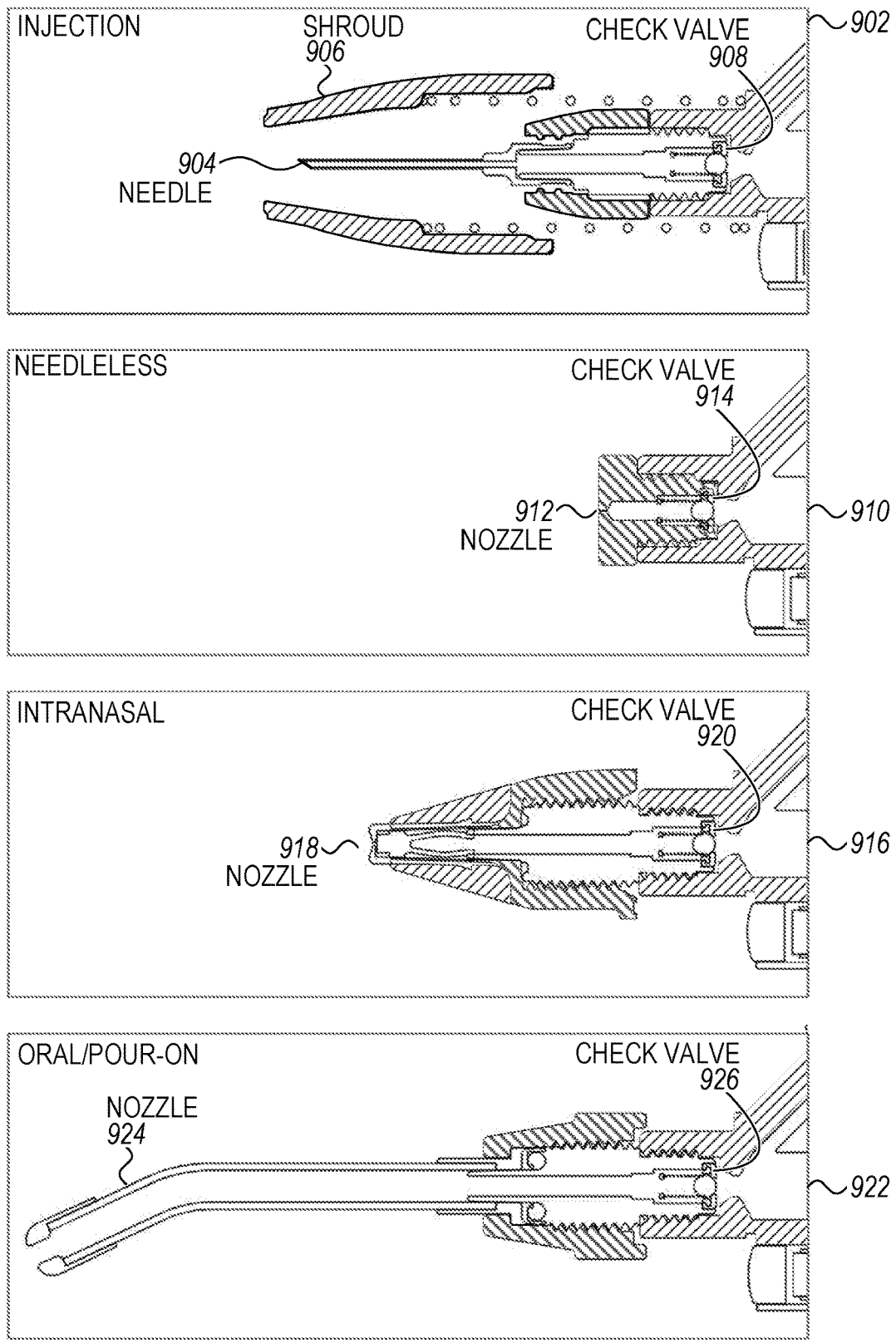
FIG. 9 contains several illustrations of different adapters for a semi-automated dosing device.

FIG. 9 is a cutaway illustration of several different adapters that may be attached to the device of embodiment 800.

An injection adapter 902 may have a needle 904 placed behind a retractable shroud 906. The adapter 902 may have a check valve 908 illustrated.

A needleless injection adapter 910 may be illustrated with a nozzle 912, which may inject a substance through a high velocity flow of medicine. A check valve 914 is also illustrated.

An intranasal adapter 916 may show a nozzle 918 designed for applying medicines or other substances into an animal's nose. A check valve 920 is shown.

An oral or pour-on adapter 922 is illustrated with a nozzle 924 and a check valve 926.

The foregoing description of the subject matter has been presented for purposes of illustration and description. It is not intended to be exhaustive or to limit the subject matter to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments except insofar as limited by the prior art.

The invention claimed is:

1. A semiautomated automated injection device comprising:
 a controller comprising a processor;
 a trigger input;
 a user interface;
 an electric motor configured to drive a syringe plunger, said syringe plunger being drivable by said electric motor in a retraction direction to draw a substance into a syringe barrel, and further drivable by said electric motor in an injection direction to force said substance from said syringe body;

a current sensor configured to sense energy consumed by said electric motor;

a distance sensor configured to sense a linear distance moved by said syringe plunger;

said controller configured to:
- determine a length to drive said syringe plunger based on a dosage input, said length corresponding to a first dose;
- receive a first trigger signal from said trigger input and in response, cause said electric motor to cause said syringe plunger to advance in said injection direction and monitor said current sensor and said distance sensor during said advance to administer said first dose;
- compare said current and said distance to determine whether said first dose is fully administered;
- when said first dose is fully administered, cause a first notice on said user interface, said first notice indicating a successful injection; and
- when said first dose is not fully administered:
  - cause a second notice on said user interface, said second notice indicating an unsuccessful injection;
  - calculate a makeup dose based on said current and said distance;
  - receive a second trigger signal; and
  - cause said electric motor to cause said syringe plunger to advance in said injection direction and monitor said current sensor and said linear sensor during said advance to administer said makeup dose.

2. The device of claim 1, said syringe body and said syringe plunger being contained in a removeable adapter.

3. The device of claim 1, said determine whether said first dose is fully administered comprising:
- determine an expected current draw per distance traveled;
- measure whether actual current draw to said motor and actual distance traveled by said plunger are within said expected current draw per distance traveled;
- when said actual current draw and actual distance traveled are within said expected current draw per distance traveled and said distance traveled equals said length, determine that said first dose was fully administered.

4. The device of claim 1, said unsuccessful injection being due to air in said syringe barrel, said second notice further indicating said air in said syringe barrel.

5. The device of claim 1, said unsuccessful injection being due to removal of said device from an animal during said administer said first dose.

6. The device of claim 1, said unsuccessful injection being due to placement of said substance in a first layer of said animal, said first layer being one of a group composed of:
- muscle;
- fat;
- intradermal; and
- subcutaneous.

7. The device of claim 6, said second notice indicating that said placement being incorrect.

* * * * *